US012742155B2

(12) United States Patent
Vervelde et al.

(10) Patent No.: US 12,742,155 B2
(45) Date of Patent: Sep. 22, 2026

(54) AVIAN ENTEROIDS

(71) Applicant: THE UNIVERSITY COURT OF THE UNIVERSITY OF EDINBURGH, Edinburgh (GB)

(72) Inventors: Apolonia Vervelde, Edinburgh (GB); Esther Jane Nash, Edinburgh (GB)

(73) Assignee: The University Court of the University of Edinburgh, Edinburgh (GB)

( * ) Notice: Subject to any disclaimer, the term of this patent is extended or adjusted under 35 U.S.C. 154(b) by 937 days.

(21) Appl. No.: 17/624,428

(22) PCT Filed: Jul. 3, 2020

(86) PCT No.: PCT/GB2020/051607
§ 371 (c)(1),
(2) Date: Jan. 3, 2022

(87) PCT Pub. No.: WO2021/001660
PCT Pub. Date: Jan. 7, 2021

(65) Prior Publication Data

US 2022/0389388 A1 Dec. 8, 2022

(30) Foreign Application Priority Data

Jul. 4, 2019 (GB) ..................................... 1909655

(51) Int. Cl.

| | |
|---|---|
| ***C12N 5/071*** | (2010.01) |
| ***C12M 1/12*** | (2006.01) |
| ***C12M 3/06*** | (2006.01) |
| ***C12N 5/00*** | (2006.01) |

(52) U.S. Cl.
CPC ........... *C12N 5/0679* (2013.01); *C12M 23/16* (2013.01); *C12M 25/14* (2013.01); *C12N 5/0062* (2013.01); *C12N 2502/23* (2013.01); *C12N 2513/00* (2013.01); *C12N 2533/90* (2013.01)

(58) Field of Classification Search
None
See application file for complete search history.

(56) References Cited

PUBLICATIONS

Nash et al. Veterinary Research 2023 54:12 pp. 1-16 (Year: 2023).*

International Search Report and Written Opinion on PCT appln. PCT/GB2020-061607 dated Sep. 22, 2020.

Julia Y. CO et al: "Controlling Epithelial Polarity: A Human Enteroid Model for Host-Pathogen Interactions", Cell Reports, vol. 26, No. 9, Feb. 1, 2019 (Feb. 1, 2019), pp. 2509-2520.e4.

Malgorzata Pierzchalska et al: "The Three-Dimensional Culture of Epithelial Organoids Derived From Embryonic Chicken Intestine: Stem Cells, Structure, and Function" IN: "Methods in Molecular Biology". Jan. 1, 2016 (Jan. 1, 2016), Humana Press, New York , NY vol. 1576, pp. 135-144.

Mohan Acharya et al: "Production and characterization of avian cryptvillus enteroids and the effect of chemicals", BMC Veterinary Research, vol. 16, No. 1, Jun. 5, 2020 (Jun. 5, 2020).

Panek Malgorzata et al: "The formation of intestinal organoids in a hanging drop culture", Cytotechnology, vol. 70, No. 3, Jan. 25, 2018 (Jan. 25, 2018), pp. 1085-1095.

Pierzchalska' Malgorzata et al: "ProbioticLactobacillus acidophilusbacteria or synthetic TLR2 agonist boost the growth of chicken embryo intestinal organoids in cultures comprising epithelial cells and myofibroblasts", Comparative Immunology, Microbiology and Infectious Diseases, vol. 53, Jun. 21, 2017 (Jun. 21, 2017), pp. 7-18.

Yuebang Yin et al: "Organoid and Enteroid Modeling of Salmonella Infection", Frontiers in Cellular and Infection Microbiology, vol. 8, Apr. 4, 2018 (Apr. 4, 2018).

Powell, Robin and Behnke, Michael titled "WRN Conditioned Media is Sufficient for in Vitro Propagation of Intestinal Organoids From Large Farm and Small Companion Animals" Dtd May 20, 2020.

Search Report for Application No. GB1909655.1 dated May 20, 2020 (5 pages).

* cited by examiner

*Primary Examiner* — Marcia S Noble
(74) *Attorney, Agent, or Firm* — Foley & Lardner LLP

(57) ABSTRACT

There is provided an in vitro three dimensional cell construct for use as a model of the avian intestine derived from avian intestinal tissue comprising avian cells organised into intestinal villi and crypts. Suitably the construct comprises an exterior surface that mimics the apical surface of a chicken intestine. Also provided are methods of making the cell construct and use of the construct as an in vitro intestinal model system to examine an agent including, but not limited to a microbe, a vaccine, a pharmaceutical, a feed additive, a toxin, a pre-biotic, post-biotic, pre pro post biotic, therapeutic, a cell, gene construct, protein, immune-modulator, an intestinal effector agent, a candidate intestinal effector agent, cell signalling inhibitor, or cell signalling activator.

5 Claims, 11 Drawing Sheets

Figure 1. Establishment of floating chicken enteroids
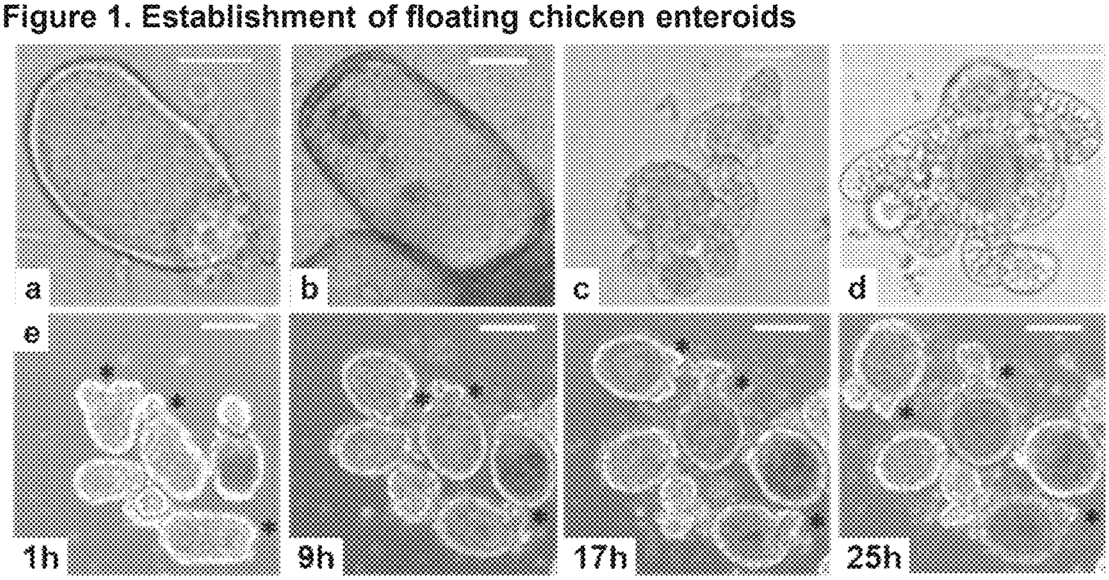

Figure 2. Reverse polarisation of avian but not mammalian floating enteroids
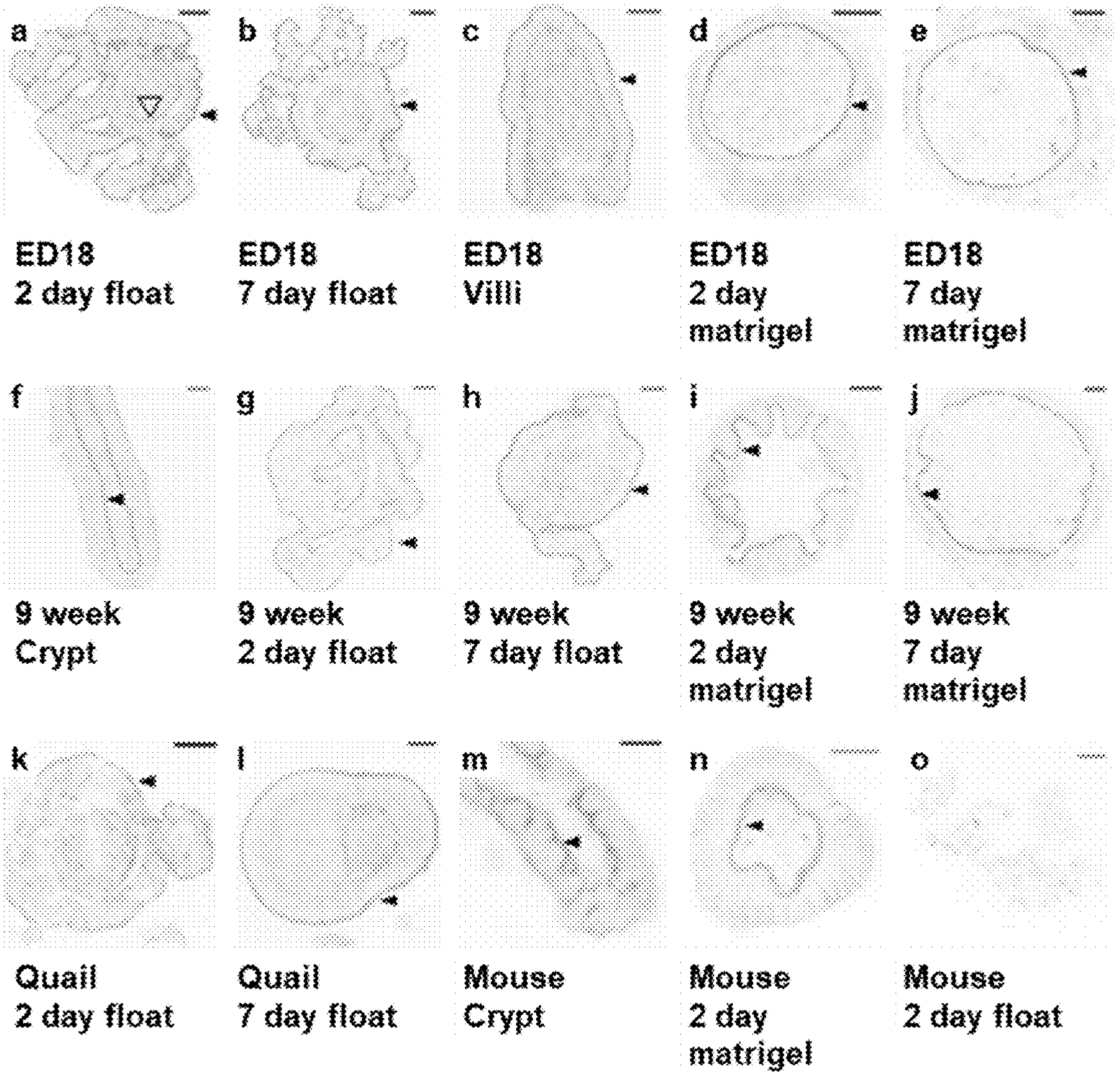

Figure 3. Multicellular composition of chicken enteroids
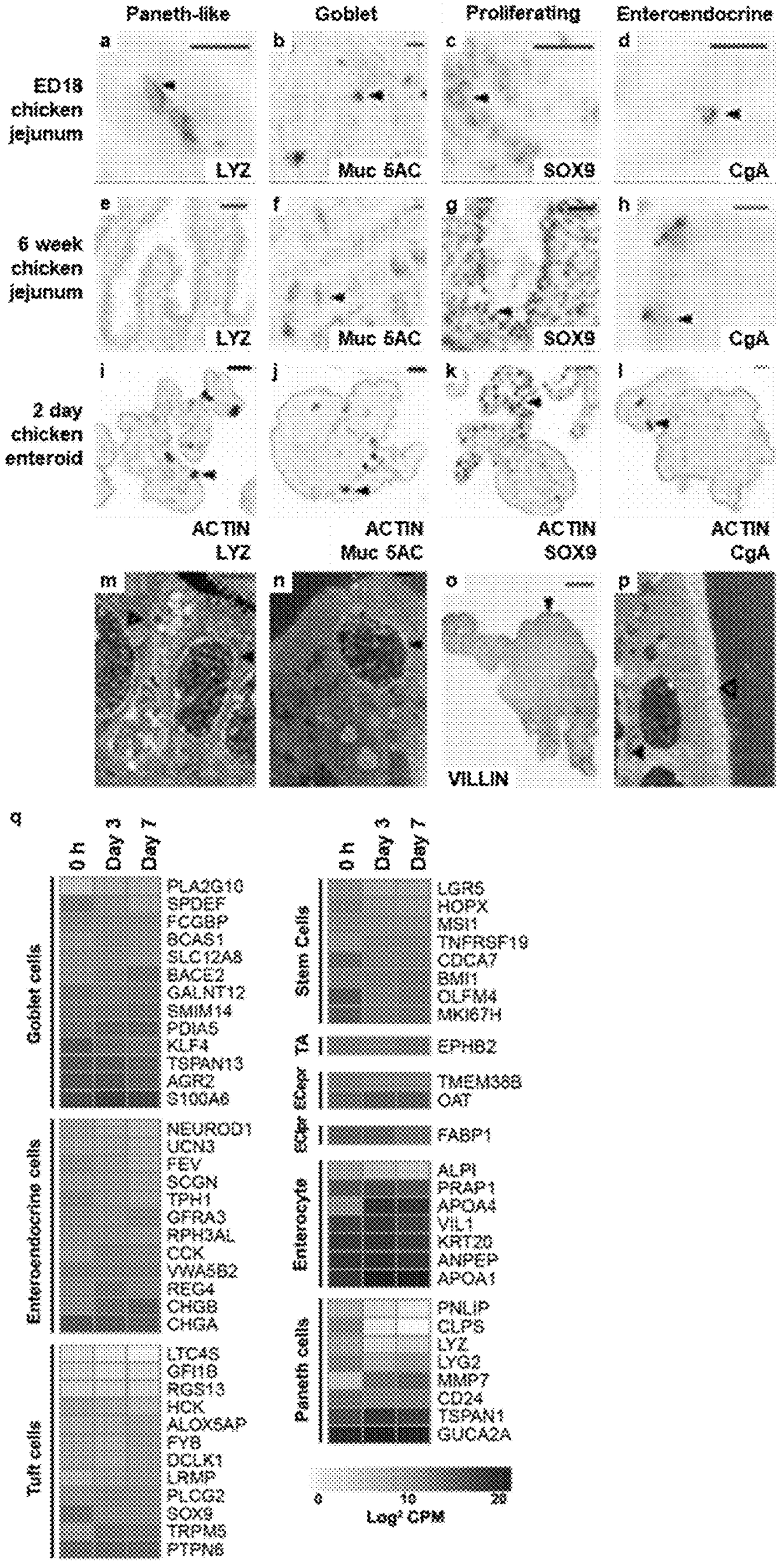

Figure 4. Site-specific chicken enteroids demonstrate multicellular composition
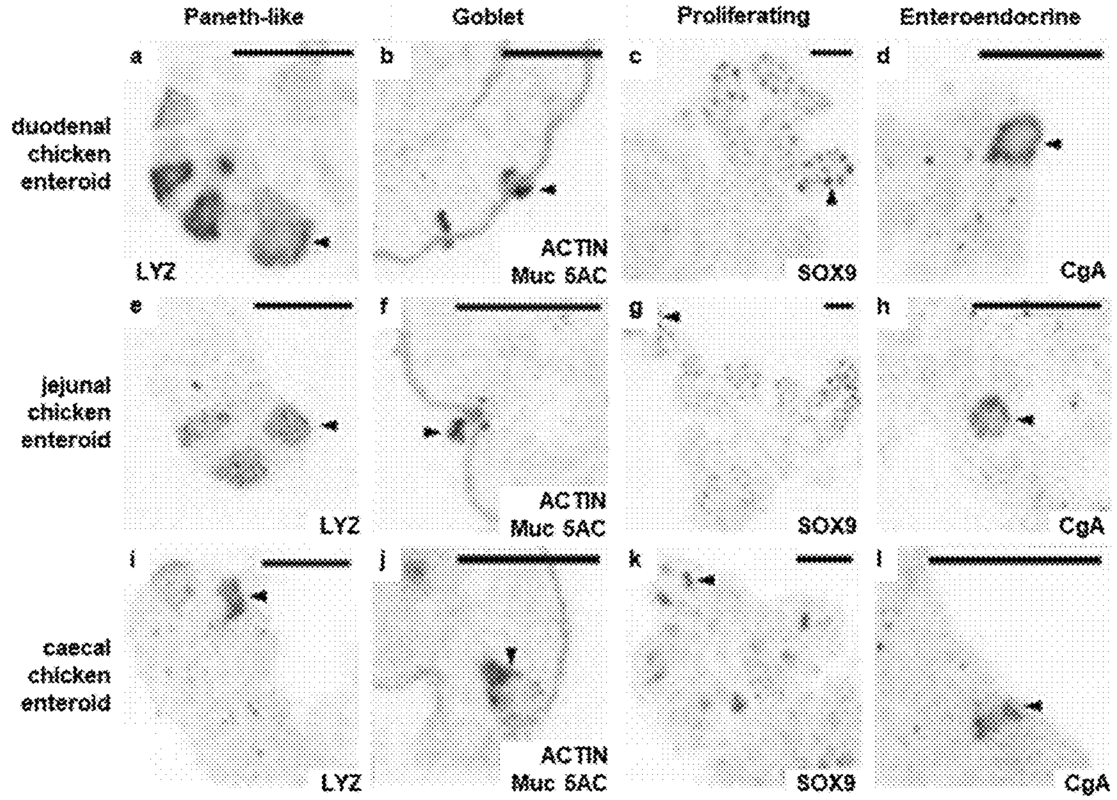

Figure 5. Chicken enteroids display epithelial barrier integrity, express cell-junction related genes and experience minimal modulation in stress-related genes
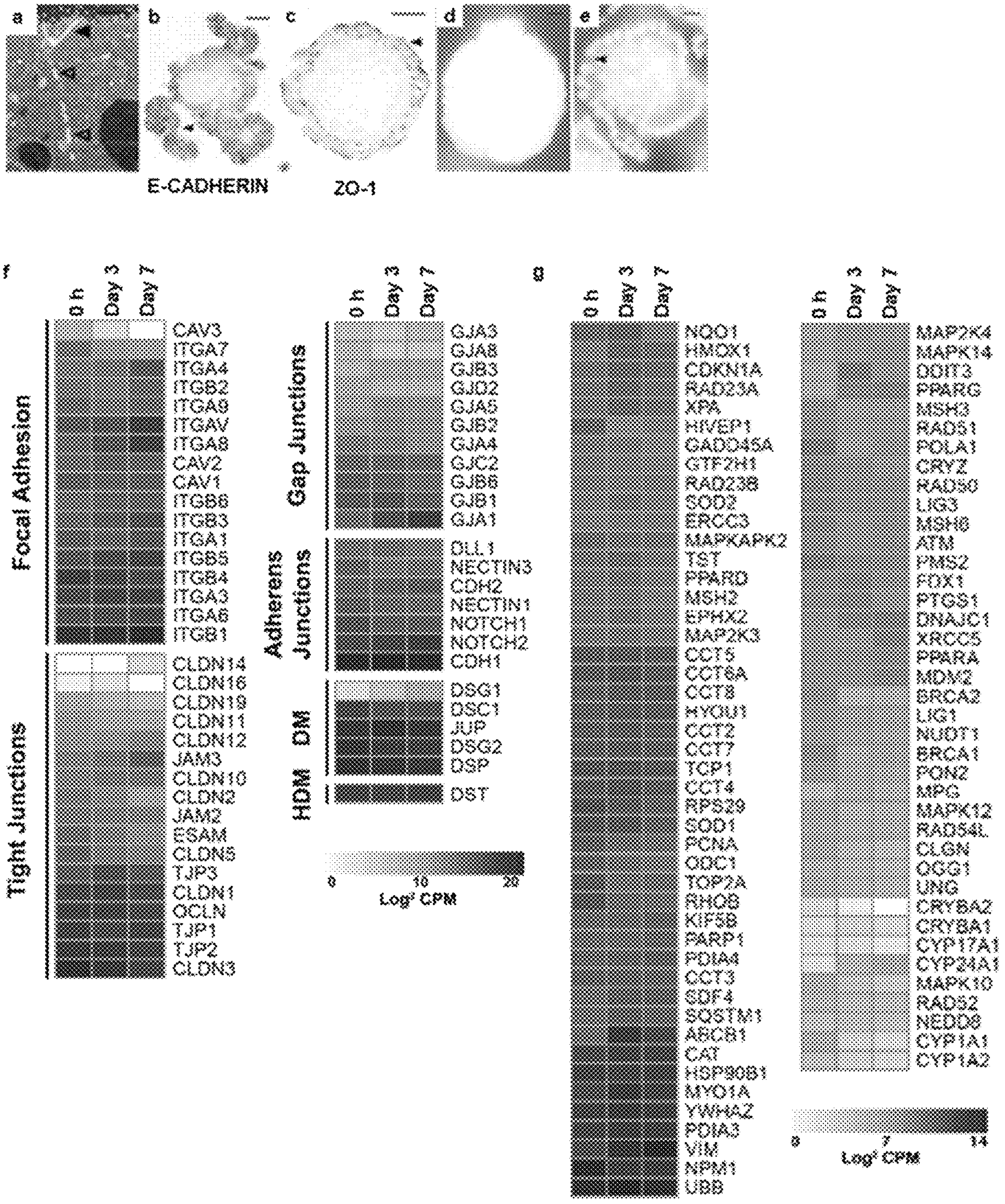

Figure 6. Immune cell component of chicken enteroids
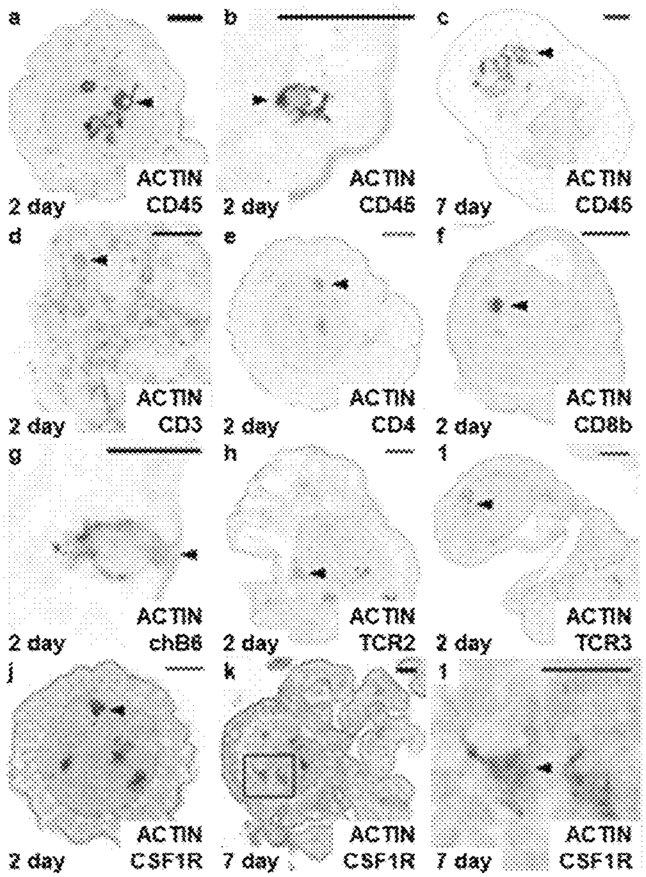
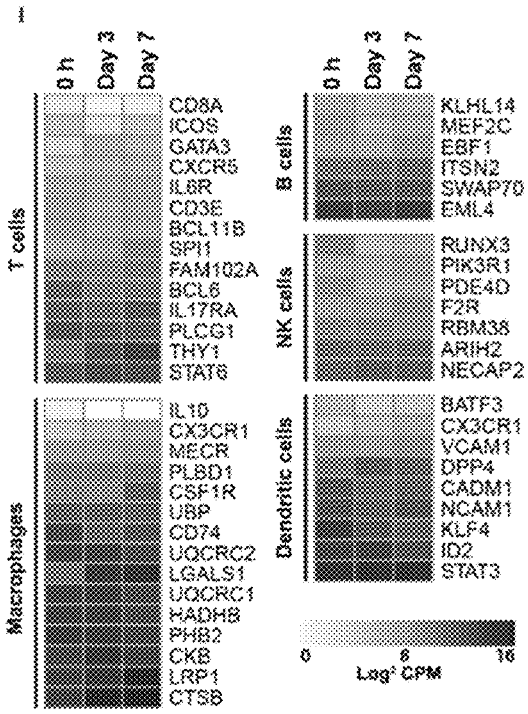

Figure 7. Chicken enteroid propagation
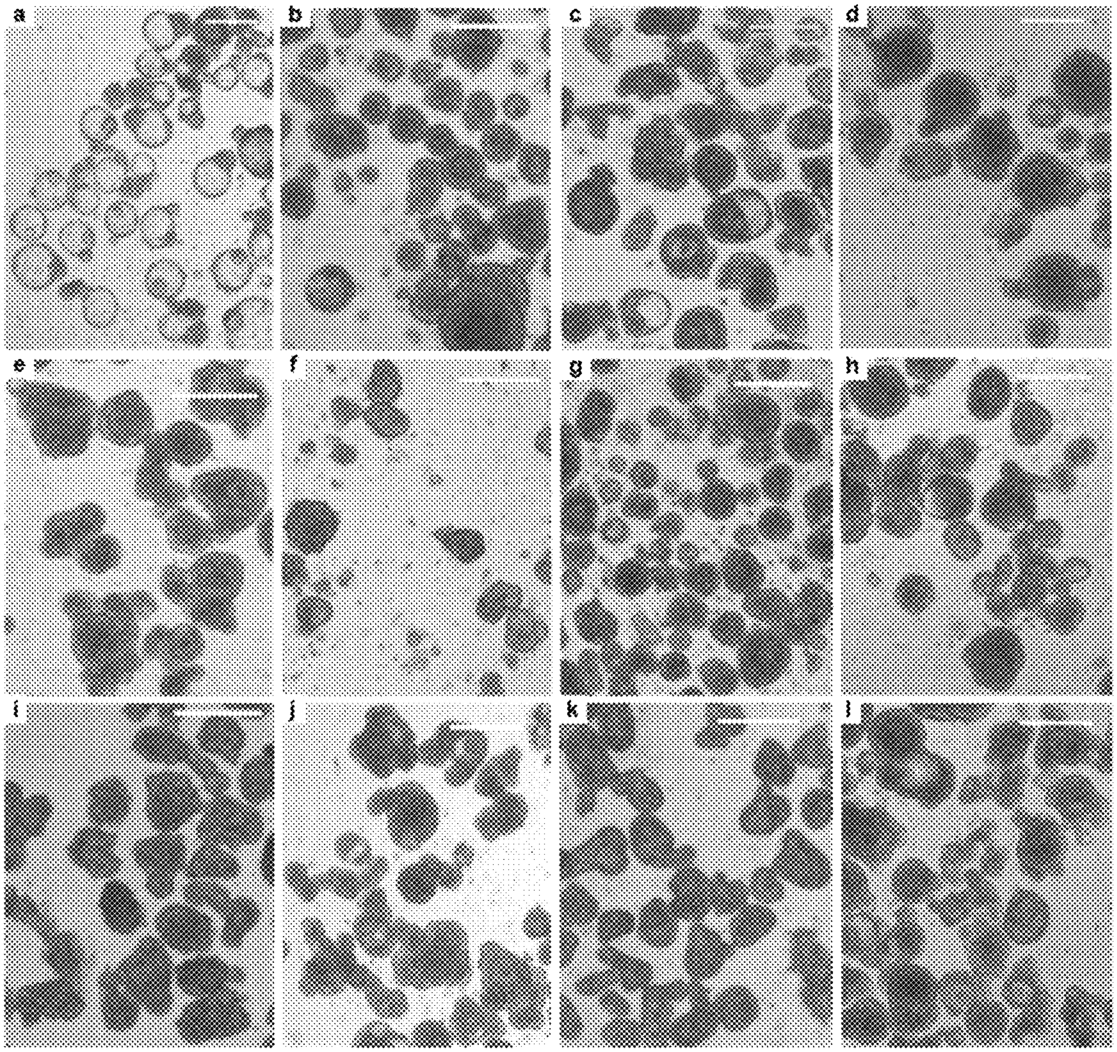

Figure 8. Chicken enteroids as a model for host-bacteria interaction
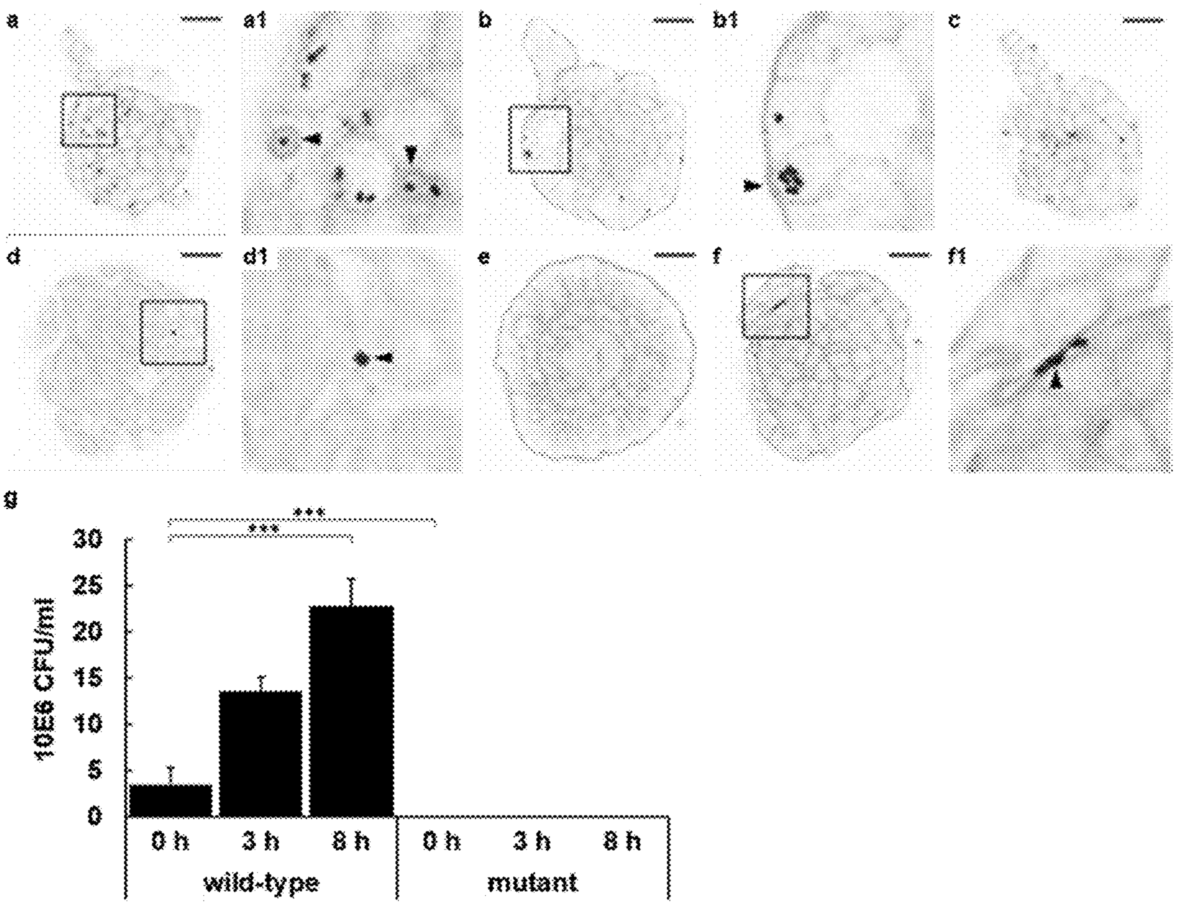

Figure 9. Chicken enteroids as a model for host-virus interaction
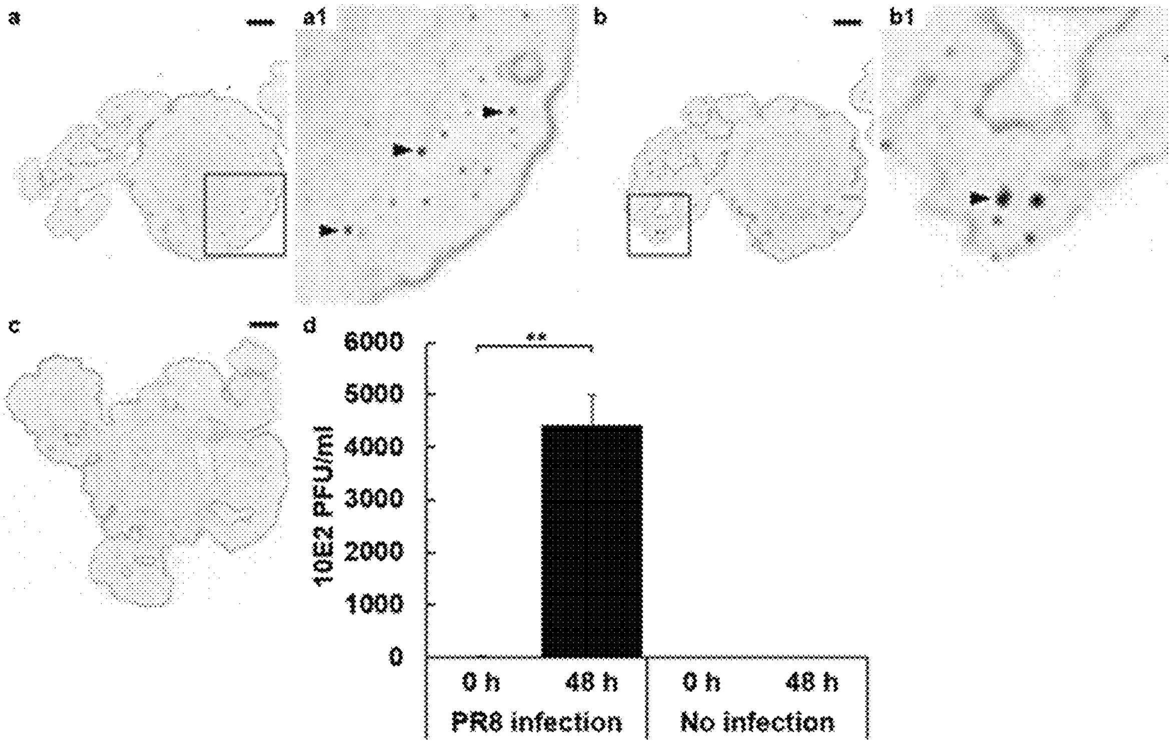

Figure 10. Chicken enteroids as a model for host-protozoal interactions
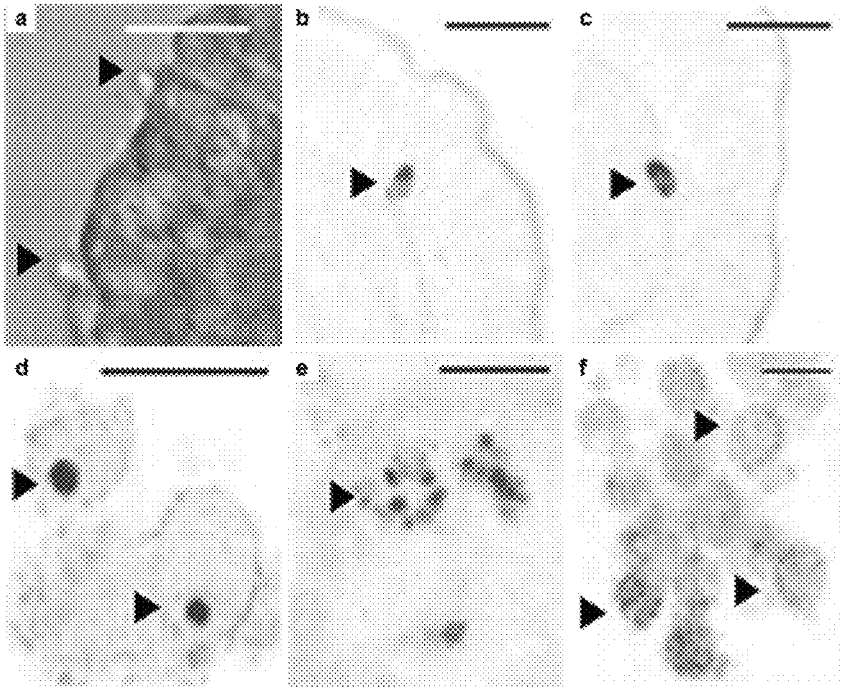

Figure 11. Development of sexual stages of *Eimeria tenella* using PCR; gamete marker EtGAM56 in infected caecal enteroid.
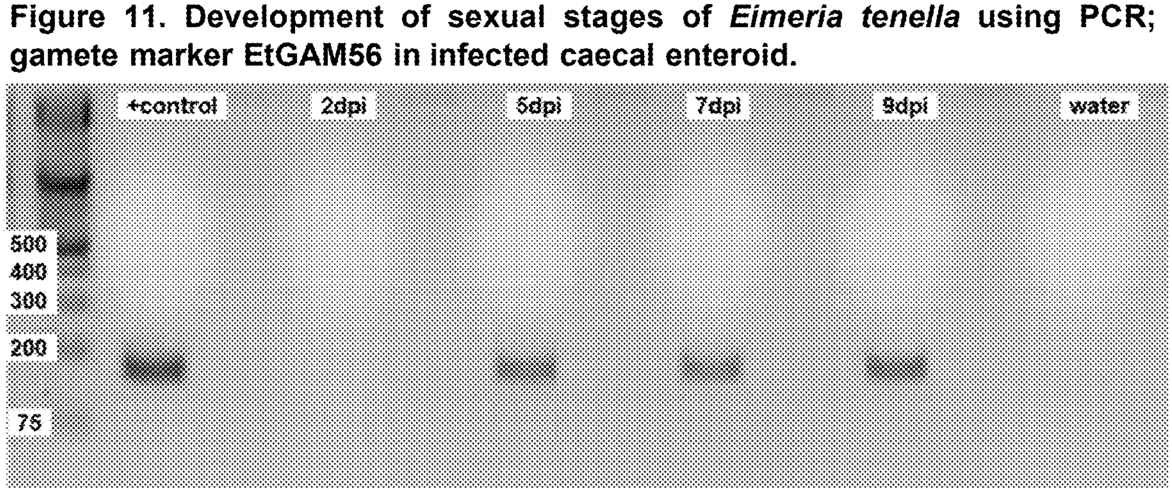

AVIAN ENTEROIDS

CROSS-REFERENCE TO RELATED APPLICATIONS

This application is a U.S. National Stage Application under 35 U.S.C. § 371 of International Patent Application No. PCT/GB2020/051607, filed on Jul. 3, 2020, which claims priority to United Kingdom Patent Application No. 1909655.1, filed on Jul. 4, 2019, the content of each of which is incorporated herein by reference in their entireties

FIELD OF INVENTION

The present invention relates to three-dimensional (3D) enteroid cultures which may for example be used in research of multicellular biological mechanisms. In particular, the present invention relates to enteroid cultures that mimic the avian in vivo intestine. Also provided is the use of the enteroid cultures to study for example cell biology, host-pathogen interactions, food science and pharmaceuticals.

BACKGROUND

Mammalian three-dimensional (3D) organoids mirror in vivo tissue organisation and are powerful tools to investigate intestinal cell biology and host-pathogen interactions. The expertise to grow continuously expanding self-organizing intestinal organoids or enteroids from mammalian adult stem cells has been developed in various mammalian species. By isolating intestinal crypts or single multipotent adult stem cells, embedding them in a gel scaffold (often an Engelbreth-Holm-Swarm tumour extract called Matrigel) and adding external defined growth factors; epidermal growth factor (EGF), R-spondin and Noggin, mammalian 3D enteroids can be generated with organized crypt and villus domains, highly polarized epithelium, functional lumen and containing all differentiated cell types at normal ratios. Crypts feed into a central lumen lined by mature epithelial cells of all villus lineages whose apical brush border domain faces inside the lumen. The basolateral surfaces, in contrast, lie in contact with the extra-cellular matrix (ECM) scaffold.

A murine culture system has been utilized for other mammals, but additional niche factors are needed to recapitulate stem cell self-renewal and differentiation hierarchy including Wnt3a, nicotinamide, molecule inhibitor anaplastic lymphoma kinase (a TGF-β inhibitor) and p38 mitogen-activated protein (MAP) kinase inhibitor.

Co et al (Cell Reports (2019) 26, 2509-2520) have provided human and murine enteroids which have a basal cell surface that faces out when grown in a gel scaffold supplemented with ECM proteins, but demonstrated that these enteroids reverse their polarity, to display the apical surface facing out, when the cell constructs are subsequently recovered from the supporting gel scaffold, transferred and cultured in suspension. Extracellular matrix proteins have been identified as one of the key regulators of this epithelial polarity change. The rapid dissociation of floating murine crypts into disorganised clumps of cells is likely due to loss of integrin signalling through basal membrane attachments. The dissociation of the cell constructs limits the utility of these constructs as a model system.

Powell et al (Biology Open (2017) 6 698-705) discusses propagation of intestinal organoids from various large farm and small companion animals. Whilst this lists chicken enteroids amongst the enteroids provided, it is clear that the use of the mammalian method using matrigel and the standard growth factors Wnt3a, R-spondin-3, and Noggin (WRN) taught therein resulted in spheroids and not enteroids being provided. Pierzchalska et al (Methods in Molecular Biology (2019) 1576: 135-144) suggests that intestinal epithelium isolated from chicken embryos in the last three days of development can be used to establish a 3D culture of intestinal organoids. However, in the method discussed therein, when fragments of epithelial tissue are embedded in Matrigel matrix on cell culture inserts, the formation of empty spheres covered by epithelial cells is observed. This methodology does not or rarely forms crypt villi structures in analogy to mammalian enteroids, but instead form spheroids rather than enteroids.

Organoids readily bridge the gap between single cell culture and in vivo studies, being composed of complementary epithelium to the tissue and species of origin, amenable to same analytical techniques as cell lines, and can be subject to genetic manipulation. A practical limitation of the 3D geometry and internal lumen of intestinal mammalian organoids is that they prevent easy access to the apical epithelium. To ensure interaction with the natural site of infection, pathogens or any other agent being tested must be; microinjected into the enteroid lumen, added to disassociated cells during passage, or 2D enteroid models must be developed.

Despite successful growth of mammalian enteroids, the production of avian enteroids have so far yielded limited results. Methods using the microenvironments successful for other species have resulted in thin-walled structures with no defined crypt- and villus-like domains and these do not resemble the morphology or array of differentiated cells found in the in vivo intestine.

SUMMARY OF THE INVENTION

In order to address the need for an in vitro mini-gut model for avian species that has equivalent architecture and multi-lineage differentiation to the original in vivo intestine, the inventors investigated alternative avian stem cell isolation procedures, in particular epithelial stem cell isolation procedures, for example from intestinal lining, villi and or crypt tissue. Further alternative enteroid culture techniques have been investigated, because microenvironments successful for other species have so far yielded limited results in the production of avian enteroids.

The term organoid can be considered as a catch-all term that can represent epithelium-only systems, and epithelium plus nonepithelial components (mesenchyme/stroma, immune cells, neurons, etc). Organoids can be derived from different sources (i.e. any primary tissue or pluripotent stem cells). Organoids are 3-dimensional structures derived from primary tissue, and grown in an artificial niche. They are structures that 'resemble an organ' and satisfy the criteria (1) 3D structure containing cells that establish or retain the identity of the organ being modelled, (2) the presence of multiple cell types, as in the organ itself. (3) self-organization according to the same intrinsic organizing principles as the organ itself. Cultures developed from inducible pluripotent stem cells are typically termed inducible intestinal organoids.

Primary cultures developed from isolated primary gastointestinal tissue or stem cells that form 3-dimensional structures mimicking the villus and crypt domains comparable to the architectures of the in vivo intestine are termed enteroids or intestinal organoids. In contrast spheroids are typically considered to be primary cultures developed from isolated intestinal tissue or stem cells that lack 3 dimensional structures mimicking the villus and crypt domains and are therefore not comparable to the architectures of the in vivo intestine.

Pierzchalska et al despite using the term organoids to discuss the hanging drop cultures therein, also refer to these cultures as spheroids or epithelial spheres as they acknowledge that the cultures do not contain the multiple cell types as in the organ itself i.e goblet, paneth, enteroendocrine cells.

Attempting to grow chicken enteroids in the microenvironments that were previously successfully used for other species, yielded limited results for avians, revealing thin-walled structures with no defined crypt- and villus-like domains. Using conventional techniques, avian intestinal 18 embryonic day (ED) villi seeded in Matrigel quickly formed spheroid structures that increased in size over 7 days of culture; however, the architecture remained basic with no obviously defined crypt-villus development. Neither these spheroids nor primary chicken intestinal monolayers resemble the morphology and array of differentiated cells found in the in vivo intestine.

The inventors have determined a method for providing multilobulated 3D avian enteroids comprised of multiple differentiated intestinal cell-types. Suitably they comprise both epithelial and mesenchymal lineages. The enteriods can be considered to resemble an organ in that they have a 3D structure that contains cells that provide the identity of the organ of being modelled, they have multiple cell types as in the organ itself and self organise according to the organising principles of the organ. By omitting the Matrigel and simply floating the chicken villi/crypts in media alone, enteroid morphology dramatically improved, indicating to the inventors a component of the matrix is responsible for inhibiting enteroid budding. In particular, in contrast to previous methods in which enteroids reverse their polarity to become apical out, the present method does not necessitate prior culturing in matrigel, subsequent recovery and resuspension. Suitably, in the present method, the enteroids are grown in suspension apical surface out. The enteroids comprise villus-crypt structures that can maintain the cellular diversity, polarity and barrier function present within an avian intestinal epithelium in vivo. In particular, the inventors have determined a method for providing enteroids from isolated avian tissues using intestinal epithelial stem cells. Suitably the intestinal epithelial stem cells may be isolated from villi and/or crypt tissues. Suitably, the intestinal epithelial stem cells may be isolated from intestinal fragments containing stem cells. Suitably the stem cells may be isolated from embryonic intestinal epithelial tissue. Suitably the stem cells may be isolated from embryonic intestinal lining, in particular villi or crypt intestinal epithelial tissue. Alternatively the stem cells may be isolated from neonate, juvenile or adult intestinal epithelial tissues.

The avian intestine can be subdivided in 5 functional domains along the proximal-to-distal axis; duodenum, jejunum, ileum, paired caeca, and a short colon that opens into the cloaca. The innermost layer of the intestinal luminal surface consists of a single cell thick epithelial lining which is organised into crypts and villi and, in the chicken, renews every 3-4 days.

Accordingly, a first aspect of the present invention provides an in vitro cell construct (enteroid) useful as a model of the avian intestine comprising avian cells organised into intestinal villi and crypts.

Suitably the cell construct of the invention may be a complex multilobulated 3D avian enteroid comprised of multiple differentiated cell-types, from intestinal embryonic villi and adult crypts.

Suitably the cell construct is a complex multilobulated 3D chicken enteroid comprised of multiple differentiated cell-types. Suitably the construct may be derived from intestinal stem cells. Suitably the intestinal epithelial stem cells may be isolated from villi and/or crypt tissues. The intestinal epithelial stem cells may be isolated from intestinal fragments containing stem cells. Suitably the stem cells may be isolated from embryonic intestinal epithelial tissue. Suitably the stem cells may be isolated from embryonic intestinal lining, in particular villi or crypt intestinal epithelial tissue. Alternatively the stem cells may be isolated from neonate, juvenile or adult intestinal epithelial tissues.

The inventors have developed avian enteroids with villus-crypt structures that maintain the cellular diversity present within, for example the chicken intestinal epithelium in vivo.

Histological and transcriptional analyses show these cultures may comprise for example intestinal stem cells, enterocytes, Paneth cells, goblet cells enteroendocrine cells and trans amplifying and Tuft cells and combinations of these cells. Suitably the enteroids may comprise intestinal stem cells, enterocytes, Paneth cells, goblet cells and enteroendocrine cells, in addition to leukocytes, as determined by histological and transcriptional analyses.

In embodiments, the inventors have developed enteroids which display a unique reverse architecture where a continuous layer of epithelial cells are polarised such that their apical surfaces face the media in which the enteroids are provided. This allows parts of the intestine to be modelled. The enteroids can be cultured in this unique reverse architecture which allows the use of these enteroids as a model system. In particular this “inside-out” phenotype allows for inexpensive and uncomplicated techniques to research host-pathogen interactions and allow pharmaceutical, nutritional and developmental studies. This contrasts constructs that are first grown in collagen gel scaffolds, and subsequentlyundergo a change in epithelial polarity, such that the apical surface faces out, when the cell constructs are recovered from the supporting collagen gel and subsequently transferred to and grown in suspension. Suitably the enteroids of the present invention may have functional integrin signalling.

Suitably enteroids of the present invention comprise an ‘inside-out’, leukocyte-containing, enteroid structure. These can provide a physiologically-relevant in vitro system that can be readily applied to study complex host-pathogen interactions in the avian gut.

Suitably the cell construct comprises:

(a) a core (b) an exterior comprising an apical epithelial cell surface.

Suitably the apical epithelial cell surface has a morphology comprising of villi and crypt structures. Suitably the apical epithelial cell surface comprises a brush border (villus like epithelium).

Suitably the exterior surface of the cell construct comprises an apical epithelial surface comprising naturally occurring differentiated cell types found in avian gut tissue. Suitably the cell construct may comprise intestinal stem cells, enterocytes, Paneth cells, goblet cells and enteroendocrine cells bound by cell-cell junctions.

Suitably the core may comprise cells from the lamina propria of the villus.

This reverse architecture (or inside out) of the enteroid structure (inside out relative to the enteroids provided by mammalian 3D enteroid structures using matrigel described to date) allows simpler modelling of agent interactions with the apical epithelial surface, for example host-pathogen interactions, without the need for complicated manipulation of the enteroids.

Suitably the construct may comprise live cells of a chicken, turkey, duck or quail or other avian.

Suitably the cell construct (enteroid structure) comprises substantially all, advantageously all, differentiated cell types typically found in an avian gut. In embodiments the cell construct can provide a surface that mimics the apical surface of a chicken intestine. This surface may be provided as a surface that surrounds an internal luminal space of the enteroid structure.

In embodiments, the cell construct provides an exterior surface—facing the media—that mimics the apical surface typically provided in an internal luminal space of mammalian intestine enteroid structures. It is considered such embodiments are advantageous as they allow easier access to the surface that mimics the apical surface of a chicken intestine.

Suitably in embodiments the cell constructs do not comprise immortalised cells.

The inventors have determined methods to isolate intestinal tissue, for example villi tips and/or crypts and derive differentiated enteroids with an accessible apical epithelial layer, suitably a 3D enteroid with an accessible apical epithelial layer that does not require either microinjection into an enteroid lumen, or dissociation of cells, or changing the polarity of 3D enteroids or organoids grown in matrigel. The inventors have determined that such methods provide enteroids that reflect the 3D architecture and cellular composition of their in vivo counterparts. Thus effective in vitro models of the chicken intestinal epithelium can be provided. Further, the inventors have determined that such enteroids can be successfully infected with microorganisms including bacteria (such as but not limited to *Salmonella Typhimurium*), viruses (such as but not limited to Influenza virus A) and parasites (such as but not limited to *Eimeria tenella*) evidencing their flexible use in the study of microorganisms of importance to human and animal health. Advantageously the unique 'inside-out' phenotype and basic growth conditions of embodiments of these enteroids is considered to allow for inexpensive and uncomplicated techniques to research host-pathogen interactions, vaccines, pharmaceuticals, feed additives, toxicology and nutritional and developmental studies.

Typically, mammalian enteroids are grown in a gel scaffold. However, the inventors have determined a method wherein the avian cell constructs, in particular chicken and quail, (enteroids) grow floating in media i.e. without structural support.

According to a second aspect there is provided a method of growing the cell construct of the invention, an avian enteroid, the method comprising the steps a) providing isolated cells from intestinal tissue from avians to culture media to provide culture media with seeded cells, b) expanding the seeded cells floating in the culture media to form at least one enteroid.

Suitably the method provides for expanding a single proliferative intestinal cell of an avian, suitably a single stem cell, suitably a population of stem cells or a tissue fragment, to generate an enteriod. Suitably the method provides for a cell construct wherein the construct has an exterior comprising an apical epithelial surface, suitably with villi-crypt structures which is in contact with the surrounding culture media.

Suitably avian enteroids may grow optimally in suspension without a structural support, for example Matrigel, required to produce mammalian enteroids. This culture environment results in an 'inside-out' enteroid conformation with media-facing apical brush borders. Histological and transcriptional analyses show these enteroids comprise of differentiated intestinal epithelial cells bound by cell-cell junctions, intraepithelial leukocytes and an inner core of lamina propria leukocytes.

Suitably the method allows culturing of 3D avian intestinal organoids in free media that recapitulate the 3D architecture and differentiated cell types of the avian gut. Advantageously, in examples of the intestinal organoids, these enteroids also display a unique morphological feature in that they are essentially "inside out" with the apical epithelial surface, with villi and crypt structures, of the enteroids in contact with the surrounding culture media. This structure is particularly advantageous as an in vitro model system for studying host/pathogen interactions, for applications in the development of vaccines, pharmaceuticals, feed additives, toxicology, nutritional and developmental studies/probiotics and for studying the impact of compounds on gut health.

Suitably there is no requirement for a solid support (for example Matrigel matrix) to be used in the method of growing the avian cell construct.

Suitably the cells are isolated intestinal cells, wherein the intestinal cells are from villi or crypts and comprise stem cells or a combination of stem cells and other intestinal cells. The specific ingredients of the culture media, and supplements thereof can be varied according to particular needs and applications.

As would be known to those of skill in the art, the seeding density, culture conditions, culture periods, can be altered as required in view of routine optimisation. Further the presence and amount of an ingredient in the culture medium and any supplement thereto can be optimised independently of any other ingredient by routine optimisation wherein one or more ingredients are added or removed. Suitably, Floating Organoid Media (FOM) may be used wherein this is provided by Advanced DMEM/F12 (Gibco) supplemented with 10 mM HEPES (Gibco), 2 mM L-Glutamine (Gibco), 50 U/ml Penicillin/Streptomycin (Merck), B27 supplement (50×) (ThermoFisher Scientific, UK).

The media for growth of the cells may be standard basal media supplemented with B27.

Suitably isolated cells or tissue may be provided from avian embryos or adult tissues. Suitably the isolated cells may be from 18 to 20 day old embryos. It is considered that provision of cells for use in the method from embryos is advantageous as they provide clean tissue fragments. Suitably cells may be provided from the intestinal villi or intestinal crypt.

In contrast to the method of the invention, seeding chicken crypts in Matrigel (as would be undertaken for mammalian enteroid growth) resulted in minimally budding spheroid structures which polarise to form a 3D architecture like their mammalian counterparts with internal microvilli and a central lumen. These hollow spheroids closely resemble murine fetal spheroids which demonstrate Wnt-dependent indefinite self-renewing properties but display a poorly differentiated phenotype (Mustata et al (2013) Cell Reports, 5 421-432). In stark contrast, in the present invention the external microvilli, extensive budding and multiple differentiated cell types of the floating chicken enteroids indicate Matrigel is not only responsible for internally polarising the organoid epithelial cells, but also for inhibiting differentiation of the chicken intestinal proliferative cells.

Suitably intestinal tissue may be isolated from the small and large intestine of avian embryos. Suitably the isolated cells may be seeded floating in a basic media composed of DMEM/F12 and B27 supplement. Suitably under growth conditions, for example in an incubator at about 37 to about 41 degrees C. and 5% $CO_2$, intestinal stem cells successfully formed enteroids, which can be visualised as 3D multilobulated structures that mimic the in vivo architecture and differentiated cell-types of the original avian intestinal epithelium.

Suitably the method comprises disrupting intestinal cells from the basement membrane to provide the isolated cells.

Suitably an enteroid may be formed within 2 hours to 24 hours using the culturing method.

Suitably the step of expanding the cells may be provided over up to 7 days. Expansion of cells is undertaken in standard growth media, for example basal media. Suitably the basal media may be supplemented with B27 during expansion of the cells.

Suitably the isolated tissue may be flat intervillus epithelium based on histology. Suitably enteroids may be developed from embryonic villus tips or crypts. Enteroid growth is considered to be possible from villus tips due to the fact that almost all cells lining the villi at this age are proliferative.

Suitably isolated intestinal tissue may be provided from villi or crypts isolated from avians, for example adult or hatched avians, for example chickens and hatched quail may be isolated and cultured is a similar manner to form enteroids.

Suitably reagents for use in the method may be used at 37° C. Suitably avian cells to be provided for use in the method may be digested with collagenase after villi or crypt isolation. Alternatively, intestinal cells can be isolated with chelating agents that release cells from their calcium- and magnesium-dependent interactions with the basement membrane and stromal cell types. After washing the tissue, the epithelial cell layer is isolated from the mucosa.

In embodiments the method can further comprise the step of freezing enteroid cells.

Without wishing to be bound by theory, it is considered the culture environment, without a support, for example matrigel, (for example when matrigel is not used at any portion of the culture process of the avian tissue isolated from intestine) causes a unique 'inside-out' conformation of the enteroids so their apical epithelial surface faces the media. The novel polarisation and growth requirements of these enteroids is considered to be advantageous as it enables contact of agents with the epithelial apical surface without requiring injection of the agent into the cell construct (as would be required in typical mammalian models), for example infection of the epithelial apical surface with infectious agents such as *Salmonella typhimurium*, Influenza virus A and *Eimeria tenella* without the need for microinjection.

Accordingly, a third aspect of the present invention provides a method of screening an agent for activity the method comprising the steps of a. providing at least one cell construct of a first aspect of the invention,
b. contacting said agent to the construct in vitro,
c. determining the activity of the agent on cells of the construct Suitably the method allows determination of host interactions with microorganisms.

Suitably the agent may be a microbe, a vaccine, a pharmaceutical, a feed additive, a toxin, a pre-biotic, post-biotic, pre pro post biotic, therapeutic, cancer cell, gene construct, protein, immune-modulator, candidate intestinal effector agent, cell signalling inhibitor, cell signalling activator, chemotherapeutic, compound, mixture, or organism, synthetic product, or a molecule or biological factor of interest. Suitably the agent may be a pharmaceutical agent or biopharmaceutical agent. Suitably the agent may be a nutritional agent. Suitably the agent may be a probiotic. Suitably the agent may be a feed additive. Suitably the agent may be at least one of a vitamin, a fatty acid, essential oil, organic acid, an enzyme and an antioxidant. Suitably the agent may be a vaccine component or agent. Suitably the agent may be provided to test for toxicology of the agent.

Suitably, a cell construct (an enteroid) of the present invention may be transduced with a viral vector. Alternatively, the method may further comprise providing CRISPR/Cas9 or the like to genetically manipulate the cell construct to express one or more genes.

Suitably a cell construct (an enteroid) of the present invention may be used to culture a microbe. Suitably the contruct may be used as a growth system for culture of pathogens and the like, for example as a growth system for organisms and pathogens presently provided in cell lines, live birds or in eggs. Suitably the cell construct mimics an in vivo gut. Suitably the microbe may be bacteria, virus, parasites, fungi or a combination thereof. Suitably the cell construct may be used to cultivate the microbe. In examples the cell construct may be used to characterise cellular processes and pathways in the gut, particularly in combination or in response to other agents. Suitably the cell construct may be used to model pathological conditions, or to develop a therapy to conditions.

Enteroids have proven to be powerful tools for a multitude of applications including developmental studies, conducting drug and feed additive screens and modelling infectious, genetic and neoplastic disease. Studies typically deliver pathogens or other substances to the apical epithelial surface. In mammalian enteroid systems of the intestine this delivery is from outside the enteroids and necessitate the use of techniques such as microinjection to introduce an agent of interest to the lumen of the enteroid.

In view of the structure of the avian enteroids provided by the inventors, with extensive budding and an externally accessible epithelial surface, modelling of mucosal host-pathogen interactions, vaccine development, pharmaceutical, feed additive, toxicological and nutraceutical screening can be conducted with comparative ease.

Suitably, the host interaction with a microorganism may be an enteroid infection. Suitably a microorganism used to consider a host interaction may be selected from a bacterium, a virus, fungi or parasitic infection, for example: *Salmonella Typhimurium*, Influenza virus A, or *Eimeria tenella*.

Suitably the method comprises a step wherein at least one live cell is labelled with a detectable compound.

In embodiments, the method may allow determination of a host interaction with an agent, for example wherein the agent is a compound, for example a proposed therapeutic compound, or dietary aid.

According to a fourth aspect of the present invention there may be provided a device for use in the method of the invention wherein the device comprises:

a. a microfluidic device comprising a chamber and at least a first channel in fluid communication with the chamber,
b. a cell construct as discussed herein and optionally,
c. growth media in the chamber, According to a fifth aspect of the present invention there is provided a method of growing a cell construct of the first aspect of the invention, the method comprising a. providing a device of the fourth aspect of the invention
b. providing growth media into the chamber at first time point to promote growth of a cell construct as described by the first aspect, according to, for example, but not limited to, a method of the the second aspect.

Suitably, in the method at least a further agent is provided to the device at at least a second time point. In embodiments the further agent may be used to determine if a change in the cells of the cell construct occurs. Based on the observed change the effect of the further agent on the intestinal cells may be determined i.e. as a toxic agent, a beneficial agent or the like.

Suitably this provides a method to evaluate enteric disease, test therapeutic components, determine the effect of bacterial communities or the ex vivo enteroid cultures.

Suitably as used herein an enteroid may be an in vitro cell construct. Suitably the cells to be grown to provide the enteroid may be obtained from a biopsy.

According to a further aspect of the present invention, there is provided the use of an in vitro three dimensional cell construct comprising avian cells organised into intestinal villi and crypts as disclosed herein in studying microbe interactions, culturing of microbes, vaccine and pharmaceutical development, feed additive screening, toxicology studies and developmental studies, screening of pre-biotics, screening of post-biotics, screening of pre pro post biotics, and regenerative medicine. Suitably the use may be in determining the efficacy of one or more therapies for one or more medical conditions, diseases or disorders comprising the step of exposing one or more therapies to the cell construct described herein.

According to a further aspect of the present invention there is provided the use of an in vitro three dimensional cell construct comprising avian cells organised into intestinal villi and crypts as provided by any of the methods of the invention in studying at least one of microbe interactions, culturing of microbes, vaccine and pharmaceutical development, feed additive screening, toxicology studies and developmental studies, screening of pre-biotics, screening of post-biotics, screening of pre pro post biotics, and regenerative medicine or the like. Suitably a method of determining the efficacy of one or more therapies for one or more medical conditions, diseases or disorders may be provided comprising the step of exposing one or more therapies to the cell construct as provided by any of the methods as described herein. Suitably the efficacy of the one or more therapies may be monitored by assaying at least one of cell barrier integrity, assaying the gene expression of one or more genes, assaying the protein levels and/or identity of one or more proteins and/or assaying the histology, assaying the immune response of the enteroid culture. Suitably the method may comprise the step of providing one or more microbes to the enteroids as described herein.

According to a further aspect of the invention there is provided a method of providing an in vitro intestinal model system, the method comprising: providing an enteroid as described herein or as provided by a method as described herein:

Providing the enteroid with an agent

Monitoring the response of the enteroid to the agent.

In embodiments the agent can be selected from a microbe, a vaccine, a pharmaceutical, a feed additive, a toxin, a pre-biotic, post-biotic, pre pro post biotic, therapeutic, cancer cell, gene construct, protein, immune-modulator, candidate intestinal effector agent, cell signalling inhibitor, cell signalling activator, chemotherapeutic, compound, mixture, or organism, synthetic product, or a molecule or biological factor of interest. Suitably the agent may be a pharmaceutical agent or biopharmaceutical agent. Suitably the agent may be a nutritional agent. Suitably the agent may be a probiotic. Suitably the agent may be a feed additive. Suitably the agent may be at least one of a vitamin, a fatty acid, essential oil, organic acid, an enzyme and an antioxidant. Suitably the agent may be a vaccine component or agent. Suitably the agent may be provided to test for toxicology of the agent.

Suitably a candidate effector agent can be an agent known to modulate the behavior of intestinal epithelial cells and/or microbes that can be found in the intestine or it can be an agent that is to be tested to see if it can modulate the behavior of intestinal epithelial cells and/or microbes that can be found in the intestine. In some embodiments of any of the aspects, an intestinal effector agent can be a treatment or drug. In some embodiments of any of the aspects, an intestinal effector agent can be a pathogen and/or toxin. Non-limiting examples of intestinal effector agents are therapeutics, small molecules, nutriceuticals, antidiarrheals, probiotics, natural intestinal microflora and/or microbes, foods, vitamins, pathogens, and toxins. In some embodiments of any of the aspects, the intestinal effector agent can be an agent which can be administered to an avian orally.

Suitably a cell of an enteroid described herein can be contacted with one or more intestinal effector agents, e.g. one effector agent, two effector agents, or more effector agents. In some embodiments of any of the aspects, the candidate effector agent or at least two candidate effector agents can be used to determine interaction with cells of the intestine or modulation of the natural gut microflora.

Suitably the response of the cells can be measured to determine the effect of at least one candidate intestinal effector agent. Suitably the cells can be measured to detect at least one of, but is not limited to, changes in viability, morphology, cell number, transcription, translation, marker gene expression, levels of a reporter gene, metabolic rate, transport, barrier function, morphology of tight junctions, and/or permeability of the cell layer, the rate at which an intestinal effector agent is taken up by cells, metabolized by cells, secreted by cells, or crosses one or more layers of cells, and/or determining how cells metabolize an intestinal effector agent.

The methods and enteroids described herein can be used to examine or test intestinal effector agents for the purposes of; toxicology, pharmacology, drug development, therapeutics, drug delivery, protein or peptide delivery, drug metabolism, antibiotic effect, effectiveness of drug coatings, IgA transport, screening of genetically modified organisms for allergenicity and toxicity, drug-drug interaction, drug bioavailability, drug clearance, multi-organ interactions, nanotoxicology, diagnostics, nutritional applications, physiology of intestinal barrier, gastrointestinal (GI) disease models and mechanism, etiology of disease in the GI tract, wound healing, tissue regeneration, tissue engineering, intestinal homeostasis, intestinal stem cells, host-microbes interactions, microbial communities in the GI tract, microbial biofilm, and pre, pro and post biotics therapies.

Each document, reference, patent application or patent cited in this text is expressly incorporated herein in their entirety by reference, which means it should be read and considered by the reader as part of this text. That the document, reference, patent application or patent cited in the text is not repeated in this text is merely for reasons of conciseness.

Reference to cited material or information contained in the text should not be understood as a concession that the material or information was part of the common general knowledge or was known in any country.

As used herein, the articles "a" and "an" refer to one or to more than one (for example to at least one) of the grammatical object of the article.

"About" shall generally mean an acceptable degree of error for the quantity measured given the nature or precision of the measurements.

Throughout the specification, unless the context demands otherwise, the terms 'comprise' or 'include', or variations such as 'comprises' or 'comprising', 'includes' or 'including' will be understood to imply the includes of a stated integer or group of integers, but not the exclusion of any other integer or group of integers.

Preferred features and embodiments of each aspect of the invention are as for each of the other aspects mutatis mutandis unless context demands otherwise.

Embodiments of the present invention will now be described with reference to the accompanying figures by way of example only, in which FIG. 1 illustrates the establishment of floating chicken enteroids (a) Matrigel-embedded embryonic chicken spheroids increase in size but lack budding at day 1 and (b) day 7 of culture. (c) Floating large multi-lobulated chicken enteroid structures develop over 3 days and are maintained at day 9 of culture (d). Scale bar: 50 μm. (e) Time-lapse images showing the formation of budding crypt-like structures (marked by *) in floating embryonic enteroids. Images are representative of data from at least 20 independent cultures each containing 2-3 embryos. Scale bar: 100 μm.

FIG. 2 illustrates the reverse polarisation of avian floating enteroids. Confocal images of whole-mount enteroids stained to detect F-actin-expressing brush borders (arrows) and DAPI to visualize cell nuclei. a Floating embryonic chicken enteroids at 2 days showing epithelial cells polarised with the apical brush border (closed arrow) facing the media and basal lamina (open arrow) sits on a central core of cells. b Embryonic chicken enteroids at 7 days of culture showing 'inside-out' polarisation. c Tissue isolated from embryonic chicken intestine to from enteroids are villi. d Embryonic enteroids cultured in Matrigel for 2 days with epithelial cells polarised so the apical brush border is facing a central lumen. e Embryonic enteroids cultured in Matrigel for 7 days. f Isolated crypts from 9 week old chicken intestine. g Enteroids from 9 week old chickens mimic embryonic chicken enteroid polarisation at 2 days and 7 days (h) in floating culture. i Matrigel-embedded enteroids from 9 week old chickens at 2 days and 7 days (j). k Enteroids derived from 1 week old quail also show 'inside-out' polarisation at 2 days and 7 days (l) of culture. m Isolated crypts from adult mouse intestine. n Matrigel-embedded mouse enteroid with internal lumen at 2 days in culture. o Floating mouse enteroid at 2 days in culture showing dissociated crypt cells. Scale bar: 20 μm. Images a-e, and f-o are representative of 3 cultures composed of 3 chicken embryos and 1 mouse per culture respectively.

FIG. 3 illustrates the multicellular composition of chicken enteroids. Confocal images of a-d embryonic jejunum, e-h 6 week old chicken jejunum, and i-l, o embryonic chicken enteroids at 2 days of culture. All cells are counterstained with DAPI. The cells are stained for Lysozyme C (a, e, i, Paneth cells), Muc5AC (b, f, j, goblet cells), SOX9 (c, g, k, proliferating cells) and Chromogranin A (d, h, l, enteroendocrine cells) and indicated by arrows. i-l Chicken enteroids stained to detect F-actin-expressing brush border. m Transmission electron microscopy of chicken enteroids (4 h in culture) demonstrates an enterocyte (closed arrow) and Paneth cell (open arrow). n TEM of chicken enteroids (7 days in culture) demonstrates a goblet cell. o Confocal image of chicken enteroid stained for villin (arrow, epithelial microvilli). p TEM of chicken enteroid 7 days in culture, enterocyte basal lamina (closed arrow) and microvilli (open arrow). Scale bar: a-l, o 20 μm. m, n, p 2 μm. Images a-p are representative of data from at least 3 independent cultures each containing 2-3 embryos. q Expression of intestinal epithelial cell lineage-specific genes in freshly isolated villi (0 h) and enteroids at 3 and 7 days of culture compared by RNA sequencing analysis. Heat maps show the relative expression levels (log 2 counts per million reads) of a range of mammalian epithelial cell lineage-related genes. TA: transit amplifying cells, ECepr: early enterocyte precursor cells, EClpr: late enterocyte precursor cells. RNA sequencing data is representative of 3 independent experiments, each comprising of 2 technical replicates, each containing 3 embryos.

FIG. 4 illustrates site-specific chicken enteroids demonstrate multicellular composition. a-l Confocal images of embryonic chicken enteroids at 2 days of culture grown from the duodenum, jejunum and caeca. Stained for Lysozyme C (a, e, i, Paneth cells), Muc5AC (b, f, j, goblet cells), Sox9 (c, g, k, proliferating cells), and Chromogranin A (d, h, l, enteroendocrine cells) as indicated by arrows. All counterstained with DAPI (blue). b, f, j stained to detect F-actin-expressing brush border. Scale bar: 20 μm. Images are representative of data from at least 3 independent cultures, each containing 2-3 embryos.

FIG. 5 illustrates chicken enteroids display epithelial barrier integrity, express cell-junction related genes and minimally alter stress-related genes. a Transmission electron microscopy of a chicken enteroid (7 days of culture) demonstrates tight junctions (closed arrow) and desmosomes (open arrows). b-c Confocal images of chicken enteroids (2 days of culture) stained for E-cadherin (b adherens junctions) and ZO-1 (c tight junctions) as indicated by arrows and counterstained with DAPI. d Confocal images of chicken enteroids (2 days of culture) immersed in FITC-dextran 4 kDa showing epithelial barrier integrity in untreated (d) and loss of barrier integrity after EDTA-treatment (e). Scale bar: a 2 μm, b-e 20 μm. Images are representative of data from at least 3 independent cultures each containing 2-3 embryos. f-g Expression of epithelial cell junction-related genes (f) and cell stress-related genes (g) in freshly isolated villi (0 h) and chicken enteroids at 3 and 7 days of culture was compared by RNA sequencing analysis. f Heat maps show the expression levels (log 2 counts per million reads) of a range of epithelial cell junction-related genes. DM: desmosomes HD: hemi-desmosomes. g Heat map shows minimal change in expression levels of a range of mammalian cell stress-related genes over 7 days of culture. RNA sequencing data is representative of 3 independent experiments comprising 2 technical replicates each containing 3 embryos.

FIG. 6 illustrates the immune cell component of chicken enteroids. Confocal images of chicken enteroids stained for leukocyte markers (arrows) at 2 or 7 days of culture (a-i). All enteroids are counterstained with DAPI and Phalloidin. a-c Enteroids stained for CD45 showing leukocytes in the lamina propria and epithelium (b). Enteroids at 2 days of culture stained for CD3 (d), CD4 (e), CD88 (f), chB6 (g), TCR2 (h; chicken $\alpha\beta_1$ TCR), and TCR3 (i, chicken $\alpha\beta_2$ TCR). Enteroids cultured from CSF1R-eGFP transgenic embryos at day 2 (j) and day 7 (k1 magnification of k) of culture. Scale bar: 20 µm. Images are representative of data from at least 3 independent cultures each containing 2-3 embryos. l Expression of immune cell-related genes in freshly isolated villi (0 h), 3 day and 7 day chicken enteroids was compared by RNA sequencing analysis. Heat maps show the expression levels (log 2 counts per million reads) of a range of immune cell-related genes. RNA sequencing data is representative of 3 independent experiments each comprising of 2 technical replicates each containing 3 embryos.

FIG. 7 illustrates chicken enteroid propagation. a Brightfield images of representative enteroid cultures supplemented with EGF, R-spondin and Noggin at day 1 and (b) day 9 compared to FOM-only at (c) day 1 and (d) day 9 of culture. Chicken enteroids at (e) day 4 culture, (f) immediately post-passage and (g) day 3 post-passage in plain and (h) growth factor supplemented media. Cryopreserved crypts at (i) point of thaw and (j) after 4 days of culture compared to (k) freshly isolated crypts then (l) cultured for 4 days. Images a-i are representative of at least 3 independent cultures each containing 2-3 embryos. Scale bar: 200 µm.

FIG. 8 illustrates chicken enteroids as a model for host-bacterial interactions a-f Representative z-axis projections of chicken enteroids 2 days in culture whole-mount stained to detect cell nuclei (DAPI) and F-actin-expressing brush border. Enteroids incubated with a-c wild type *S. Typhimurium*-GFP (arrows) and d-f mutant non-invasive *S. Typimurium*-GFP (arrows) at 4 hpi. Magnified images of al actin remodelling, 131 intracellular bacteria and dl, f1 lack of actin remodelling and intracellular bacteria. Images are representative of data from at least 3 independent cultures each containing 2-3 embryos. Scale bar: 20 µm. g Bacterial net replication assay confirmed *Salmonella* counts were significantly increased for enteroids infected with wild-type versus mutant *Salmonella* strains. ***$p<0.0002$, W=55, 95.5% CI for n1-n2 is (−419850, −189760) using a Mann-Whitney U test (two-sided). The assay also showed wild-type *Salmonella* replicated in the enteroids over 0-8 h. ***$p<0.0001$, $R^2=0.73$, df=29 using a linear regression test. Bars represent bacterial count from −800 infected enteroids post high-dose gentamicin treatment. Data represent mean±SD derived from 5 independent experiments with 2-3 embryos per culture.

FIG. 9 illustrates chicken enteroids as a model for host-viral interactions a-b Representative z-axis projections of chicken enteroid 3 days in culture whole-mount stained to detect cell nuclei (DAPI), F-actin-expressing brush border and virus nucleoprotein (arrows) after incubation with influenza A virus (PR8) for 24 h. a1 Magnified image of a. and b1, which is Magnified image of b. c Isotype control. Images are representative of data from at least 3 independent cultures each containing 2-3 embryos. Scale bar: 20 µm. d Bars represent viral titers, determined by plaque assay in supernatant from −800 infected enteroids at 0 and 48 hpi. Data represent mean±SD derived from 4 independent experiments each containing 2-3 embryos and ~800 seeded enteroids/well. **$p<0.001$, T=−14.98, 95% CI for mean difference (−514720, 334344), df=3 using a paired t-test (two-sided).

FIG. 10 illustrates chicken enteroids as a model for host-protozoal interactions a Brightfield image of sporozoites (arrows) entering caecal enteroid at 1 dpi. b-f Representative z-axis projections of chicken caecal enteroids whole-mount stained to detect cell nuclei (DAPI), F-actin-expressing brush border after incubation with PKH-67 labelled *E. tenella* (arrows). b Sporozoite at 2 dpi within enteroid epithelial cell and (c) migrating through basement membrane into lamina propria. d *E. tenella* trophozoite-like structures. e-f Schizogeny within enteroid epithelial cell at 9 dpi. Scale bar: a-d, f 20 µm, e 10 µm. Images are representative of data from 2 independent experiments each with 2-3 technical replicates containing>3 embryos.

FIG. 11 illustrates development of sexual stages of *Eimeria tenella* using PCR of gamete marker EtGAM56 in infected caecal enteroid. Positive (+) control is chicken caecal tissue from 6 dpi and 13 dpi after in vivo infection with *Eimeria tenella*. Caecal enteroids were infected with *Eimeria tenella* for 2 days, 5 days, 7 days and 9 days. Band at 178 bp where EtGAM56 expected in positive control as well as 5, 7 and 9 dpi. No band evident at 2 dpi or in water control.

FIG. 12 illustrates the induction of proinflammatory cytokine IL-6 mRNA after inoculation of 3D enteroids with wild type (w/t) *Salmonella Typhimurium* and a non-invasive mutant strain defective in the *Salmonella* pathogenicity island 1 (SPI1)-encoded T3SS.

FIG. 13 illustrates that incubation of 3D enteroids with the TLR4 ligand LPS (lipopolysaccharides derived from *Salmonella enterica*) induces modest upregulation of proinflammatory cytokines IL-6 but not IL-8 mRNA at 6 hours post stimulation.

DETAILED DESCRIPTION OF THE INVENTION

Examples

Example 1—Animals

Experiments were performed using ED18 to 9 week old Hy-Line Brown chickens (*Gallus* gal/us), ED17 CSF1R-eGFP transgenic chickens and 2 day old quail (Coturnix coturnix) obtained from the National Avian Research Facility, Edinburgh, UK. Five month old C57BL/6 mice were provided by the Biological Research Facility, University of Edinburgh, UK. All animals were housed in premises licensed under a UK Home Office Establishment License in full compliance with the requirements of the Animals (Scientific Procedures) Act 1986 and with approval from The Roslin Institute Animal Welfare Ethics Review Board.

Example 2—Isolation of Avian Intestinal Stem Cells Containing Tissue

The small intestine was removed post-mortem, cut open longitudinally then into 5 mm sections and collected into $Ca^{2+}$- and $Mg^{2+}$-free Phosphate-buffered saline (PBS) and washed. The tissue was digested in Dulbecco's Modified Eagle's Medium (DMEM) (Thermo Fisher Scientific) with 0.2 mg/mL Collagenase from *Clostridium histolyticum* Type IA (Merck) at 37° C. The tube was shaken vigorously, tissue allowed to settle then supernatant collected. These steps were repeated to generate 4 fractions. Fractions were centrifuged at 100×g for 4 min and tissue integrity assessed. The crypts/villi were counted and resuspended in FOM at ~200/mL; Advanced DMEM/F12 (Thermo Fisher Scientific)

supplemented with 10 mM HEPES (Thermo Fisher Scientific), 2 mM L-Glutamine (Thermo Fisher Scientific), 50 U/mL Penicillin/Streptomycin (Merck) and 2% B27 supplement (50×; Thermo Fisher Scientific). Where indicated the enteroid cultures were supplemented with 25 ng/mL EGF (Prepotech), 25 ng/mL Noggin (Enzo Life Sciences), 250 ng/mL R-spondin (R&D Systems), 100 mM Y-27632 (Cambridge Bioscience), 100 mM SB202190 (Enzo Life Sciences) and 5 mM LY2157299 (Cambridge Bioscience). Differentiation of avian enteroids occurred at 37° C., 5% $CO_2$ with media changed every 2 days. For duodenal, jejunal, caecal and quail enteroids the isolation and culture protocols were kept the same.

To seed chicken intestinal crypts/villi in Matrigel (Corning), the isolated material was resuspended in equal volumes of FOM and ice-cold Matrigel to allow for 50 per 50 μL and cultured as described for mouse intestinal crypts, using FOM instead of Intesticult medium (Stemcell Technologies).

Example 3—Infection of Organoids

Infection of Enteroids with *Eimeria tenella* Sporozoites

Frozen purified *Eimeria tenella* sporozoites were washed in warm DMEM and labelled with PKH67 Green Fluorescent Cell Linker kit (Sigma-Aldrich) according to manufacturer's protocol. ~5×$10^4$ sporozoites were added to each well containing fifty 2 day old chicken enteroids. These were incubated at 37° C., 5% $CO_2$. Fresh caecal enteroids, cultured for 2 days, were added to the cultures at 4 and 6 dpi to provide fresh epithelial cells for the merozoite stages. Enteroids were collected for analysis at 1, 2, 4, 7 and 9 dpi.

Infection of Enteroids with *Salmonella Typhimurium*

*Salmonella enterica* subspecies *enterica* serovar *Typhimurium* strain 4/74 carrying a chromosomal pFVP25.1::gfp fusion linked to the naladixic acid resistance gene was utilised for infections of the chicken enteroids and compared to a defined mutant, ST4/74 $nal^R$ ΔprgH::kan. This prgH mutant is confirmed to have reduced Type 3 secretion by analysing secretion of SipC, a *Salmonella* type III secretion system effector protein, and was also transformed with the plasmid pFVP25.1 which constitutively expresses GFP. Strains were cultured overnight in Luria-Bertani (LB) broth with 50 μg/mL kanamycin (not used for wild-type ST4/74 $nal^R$), 50 μg/mL ampicillin and 20 μg/mL naladixic acid at 37° C. Wells containing 50 enteroids were inoculated with 5×$10^4$ bacteria in antibiotic-free FOM and incubated statically at 37° C., 5% $CO_2$ before samples were collected at 0.5 and 4 hpi for analysis. Bacterial replication was measured by incubating enteroids with the *Salmonella* strains at 37° C., 5% $CO_2$ for 1 h, then high-dose gentamicin (50 μg/mL) was added to the wells for 30 min. Enteroids were washed and incubated with low-dose gentamicin (10 μg/mL) added to FOM (without Penicillin/Streptomycin). Enteroids were collected at 0, 3 and 8 h post high-dose gentamicin treatment and disrupted using steel beads in a Tissue-Lyser. Serial dilutions were plated on naladixic acid containing LB agar in duplicate and incubated at 37° C. overnight.

Infection of Enterioids with Influenza Virus A

Fifty enteroids were incubated with 2×$10^7$ PFU H1N1 virus (A/Puerto Rica/8/34 (PR8) in DMEM supplemented with 50 U/mL Penicillin/Streptomycin and 50× v/v B27 at 37° C., 5% $CO_2$ for 1 h. Control cultures either had PBS or allantoic fluid from uninfected chicken eggs added to the media. The enteroids were then washed and reseeded in DMEM media supplemented with 2 μg/mL TPCK-trypsin and collected at 48 hpi for analysis. Supernatants were harvested at 0 and 48 h post incubation and titrated by plaque assay on MDCK cells.

Example 4

To determine the structure and composition of the cell constructs provided, a number of methods were utilised.

Transmission Electron Microscopy (TEM)

Enteroids were fixed in 3.0% glutaraldehyde in 0.1 M sodium cacodylate buffer, pH 7.3, for 2 hours and processed as described as would be known in the art. Ultra-thin sections (60 nm) were stained in uranyl acetate and lead citrate and imaged using a JEOL JEM-1400 Plus TEM. Images were analysed using ImageJ (Fiji).

Whole Mount and Immunohistochemical (IHC) Staining

Details of the sources, clone numbers and concentrations of the primary and secondary antibodies used for IHC are provided in Table 1. Enteroids were fixed with 4% paraformaldehyde then blocked with 5% v/v goat serum in permeabilisation solution (0.5% v/v bovine serum albumin and 0.1% v/v Saponin in PBS) and stained with primary and secondary antibodies at 4° C. DNA was stained with 4',6-diamidino-2-phenylindole (DAPI; Thermo Fisher Scientific) and, where indicated, F-actin was visualised with Alexa Fluor conjugated Phalloidin (Thermo Fisher Scientific). Enteroids were then mounted in ProLong® Diamond Antifade Mountant (Thermo Fisher Scientific). Isotype and negative controls were prepared for each staining.

Intestinal tissue was snap frozen in liquid nitrogen, 10 μm sections were prepared on a Leica Cryostat CM1900 and mounted on Superfrost Plus slides (Thermo Fisher Scientific). Tissues were fixed in 50% methanol then blocked and stained as described for staining of whole mount enteroids.

TABLE 1

Primary antibodies used for immunohistochemistry.

| Target | Antibody details | Clone | Catalog number | Dilution |
|---|---|---|---|---|
| Mucin 5AC | Mouse anti-mucin 5AC [a] | 45M1 | Ab212636 | 20 μg/ml |
| Lysozyme C | Rabbit anti-lysozyme [a] | polyclonal | Ab391 | 20 μg/ml |
| Chromogranin A[SP1] | Rabbit anti-chromogranin A [b] | polyclonal | 20085 | 1.3 μg/ml |
| Sox9 [phospho S181] | Rabbit anti-SOX9 [a] | polyclonal | Ab59252 | 2 μg/ml |
| Villin | Mouse anti-villin [c] | 1D2C3 | Sc-58897 | 4 μg/ml |
| E-Cadherin | Mouse anti-E-Cadherin [d] | 36/E-Cadherin | 610181 | 5 μg/ml |
| ZO-1 tight junction protein | Rabbit anti-ZO1 [a] | polyclonal | Ab216880 | 10 μg/ml |
| Virus nucleoprotein | Rabbit anti-NP [e] | polyclonal | n/a | 1:1000 |
| CD45 | Mouse anti-CD45[f] | AV53 | n/a | 1:100 |
| ChB6 | Mouse anti-Bu-1[g] | AV20 | 839502 | 2 μg/ml |
| CD3 | Mouse anti-CD3[h] | CT-3 | 820009 | 2 μg/ml |

RNA Isolation and Sequencing

Enteroids from three cultures were collected at 0, 3 and 7 days of culture, lysed in RLT buffer (Qiagen) containing 10 μg/mL 2-mercaptoethanol (Sigma-Aldrich) and homogenised using Qiashredder columns (Qiagen). Each culture (biological replicate) arose from 3 pooled embryos. Two duplicate plates were cultured for each biological replicate, and samples were taken from each plate as technical replicates. RNA was extracted using the RNeasy mini kit (Qiagen) according to the manufacturer's protocol including DNase I treatment. The RNA quality and concentration was assessed using D1000 Screentape Agilent System (Agilent Technologies) then stored at −80° C. Libraries were prepared and sequenced on Illumina Novaseq 6000 by using 150-bp paired-end sequencing. Obtained reads were trimmed for quality and to remove adaptor sequences using Cutadapt. Reads after trimming were required to have a minimum length of 50 bases. Paired-end reads from Illumina sequencing were aligned to the *Gallus gallus* genome (*Gallus_gallus*-5.0) using STAR. The annotation used for counting was the standard GTF-format annotation for that reference (annotation version 91). Raw counts for each annotated gene were obtained using the featureCounts software (version 1.5.2). Differential gene expression analysis was performed within the Bioconductor edgeR package (version 3.16.5). Comparison of the embryonic enteroid transcriptome at 0, 3 and 7 days post cultivation revealed that there were no differentially expressed genes between the technical replicates (FDR<0.05), demonstrating the consistency and reproducibility of the enteroid system. The sumTechReps function in EdgeR was used to merge technical replicates. All subsequent steps were performed on the merged samples. The raw counts table was filtered to remove genes consisting predominantly of near-zero counts, filtering on counts per million (CPM) to avoid artefacts due to library depth. Statistical assessment of differential expression was carried out with the likelihood-ratio test. Differentially expressed genes were defined as those with FDR<0.05 and log FC>2. Heatmaps were constructed in R using the pheatmap package (v. 1.0.10).

Development of chicken enteroids after villi or crypt isolation using a Matrigel-based culture system resulted in poor representations of the in vivo chicken intestine (FIG. 1). Tissue fragments seeded in Matrigel quickly form spheroid structures that did increase in size over 7 days of culture; however the architecture remained basic with no obviously defined crypt-villus development.

Floating chicken enteroids demonstrate a unique 'inside-out' phenotype

Self-organising chicken and mammalian enteroids embedded in Matrigel demonstrate a single sheet of epithelial cells that are polarized so the microvilli surface is facing into a central lumen. In contrast, fluorescent staining of the embryonic floating chicken enteroids of the invention at 2 and 7 days after cultivation showed their epithelial cells had an atypical reversed polarity (FIG. 2*a, b*). The F-actin positive apical brush border could be visualised on the external epithelial surface facing the media (FIG. 2*a* closed arrow). The basal surface of the epithelial cells, in contrast, abutted a dense central cellular core (FIG. 2*a* open arrow). The inventors identified that the isolation procedure from embryonic chicken intestine resulted in collection of villus structures with an external brush border and cell-dense internal structure rather than crypts (FIG. 2*c*). In contrast, staining of digested and fractionated adult avian and mouse small intestine for F-actin showed the expected isolated crypts with an internal dense brush border (FIG. 2*f, m*).

To confirm the 'inside-out' phenomenon was unique to floating enteroids, the isolated embryonic chicken villi were seeded into Matrigel domes and imaged at 2 and 7 days of culture (FIG. 2*d, e*). At both time-points orientation of the Matrigel-embedded chicken enteroids reflected their mammalian Matrigel-embedded enteroid counterparts, with the basal cell surface polarised towards the outside, touching the Matrigel, and enterocyte brush borders forming the central luminal surface. The direction of the Matrigel-embedded enteroids' epithelial apical-basolateral polarity was in stark contrast to that of the floating enteroids (FIG. 2*a, b*).

Similar staining was performed on 2 and 7 day chicken enteroids derived from 9 week old birds to investigate if the reverse polarity was related to the age and type of progenitor enteroid tissue (FIG. 2*f-j*). Enteroids developed from the crypts of 6-9 week old chickens displayed the same phenotypes when grown in Matrigel (internal brush border) or floating (external brush border) as enteroids developed from the villi of embryos. In mature birds, the enteroids developed fewer buds and long-term viability of cultures was lower compared to those prepared from embryonic tissue.

In order to explore whether the development of 'inside-out' enteroids from floating crypts/villi was a species-specific phenomenon, F-actin staining of floating enteroids from 2 day old quail was performed at 2 and 7 days of culture (FIG. 2*k, l*). The external brush border of quail enteroids mirrored data obtained from chickens, demonstrating that formation of 'inside-out' enteroids from isolated villi in floating culture extends across at least two avian species.

The inventors then expanded the range of species analysed to explore the phenotypic plasticity of mammalian intestinal crypts in a liquid environment. Mouse crypts (FIG. 2*m*) seeded in Matrigel predictably developed into enteroids with an internally polarised lumen, forming spheroid structures by 2 days of culture (FIG. 2*n*) and multiple budding structures by 7 days. In contrast, isolated murine crypts cultured in Mouse IntestiCult medium alone failed to maintain structural integrity and at 2 days of culture no enteroid-like structures were visible (FIG. 2*o*).

Floating Chicken Enteroids Reproduce the Cellular Diversity of the Intestinal Epithelium In Vivo To investigate whether the multilobulated floating chicken enteroids displayed the array and of cell types that would be expected in vivo, immunofluorescent staining and TEM were performed at various time-points from isolation to 7 days of enteroid culture and compared with embryonic and immunologically mature chicken jejunal tissue sections.

In human and mouse small intestinal epithelium, lysozyme C is synthesized and secreted by crypt dwelling Paneth cells, in the embryonic chicken small intestine and floating chicken enteroids, lysozyme C-expressing epithelial cells were observed scattered throughout the epithelium (FIG. 3*a, i*; TEM FIG. 3*m*). Assuming chicken Paneth-like cells play a similar stem-cell supportive role as their murine counterparts, this staining pattern could also reflect the multiple sites of proliferation expected along the villi in late stage embryos and newly hatched chicks. Lysozyme C was not detected by immunohistochemistry in the 6 week old gut sections (FIG. 3*e*). This could reflect a reduction in expression with age, or, as a more recent publication has reported Lysozyme C mRNA expression up to 8 weeks post-hatch, reduction of protein expression through complex gene regulatory mechanisms. SOX9, which is expressed by stem cells, transit-amplifying cells and terminally differentiated Paneth cells, was concentrated in cells lining the embryonic villi and mature chicken crypts (FIG. 3*c, g*). Localisation of SOX9 in embryonic enteroid buds (FIG. 3*k*) indicates these villus-like structures are sites of proliferation and differentiation of intestinal stem and progenitor cells. Goblet cells (Muc5AC+ cells, FIG. 3*b, f, j*; TEM FIG. 3*n*) and enteroendocrine cells (chromogranin A+ cells, FIG. 3*d, h, l*) were scattered throughout the enteroids, and in embryonic and mature chicken gut sections. Uniformly polarized enterocytes with clear apical villin-expressing brush borders (FIG. 3*o*), external microvilli (TEM, FIG. 3*p* open arrow) and internal basal lamina (FIG. 3*p* closed arrow) lined the enteroid epithelial surface. Globally the distribution patterns of the cell types in the enteroids appeared to be similar to that observed in the embryonic intestine in vivo.

The transcriptional profile of embryonic enteroids at 0, 3 and 7 days post cultivation suggested expression of gene sets characteristically associated with mammalian Paneth cells, enterocytes, goblet cells and enteroendocrine cells (FIG. 3*q*). In addition, expression of classical markers for cell subpopulations that could not be detected by microscopy, including stem cells, transit amplifying cells and tuft cells, were identified. The expression of these genes for most cell-types was relatively stable during the cultivation period, suggesting that the enteroids accurately recapitulate the cellular diversity of the in vivo epithelium for at least 7 days.

In order to provide site-specific models for in vitro infection studies, differentiated chicken duodenal, jejunal and caecal enteroids were individually prepared (FIG. 4). Characterisation of these enteroids showed they contained a similar abundance of cell types, as well as an 'inside-out' conformation. The caecal enteroids utilised the same growth requirements as small intestinal enteroids, but developed fewer shorter buds which is reflective of the in vivo villi characteristics.

Example 5

Chicken Intestinal Organoids are Susceptible to Infection by Bacteria, Eukaryotic Parasites and Viruses Once an in vitro chicken enteroid culture system and its reversed polarisation had been established, the inventors tested if they could be infected by different classes of pathogens. The 'inside-out' phenotype facilitated uncomplicated infection studies by simply adding microorganisms to the media, using a range of important avian and zoonotic pathogens. Enteroids were incubated for 4 h with either a wild-type S. *Typhimurium* strain or a non-invasive mutant strain, defective in the *Salmonella* pathogenicity island 1 (SPI1)-encoded T3SS. S. *Typhimurium* uses effector proteins translocated by the SPI1 T3SS to induce host-cell actin remodelling on the apical surface of polarized epithelial cells. These membrane 'ruffles' are a well-characterised feature of *Salmonella* virulence, promoting internalization of the pathogen by non-phagocytic cells. After 30 min of wild-type S. *Typhimurium* incubation with enteroids, the bacteria were visualised in contact with the apical epithelial surface. At 4 hours post infection (hpi), dense actin rings surrounded individual bacteria (FIG. 8*a*1) and large numbers of bacteria were disseminated intracellularly throughout the enteroids (FIG. 8*b*1). In contrast, few non-invasive mutant S. *Typhimurium* were found in contact with the microvilli, no dense cytoskeletal modifications were visualised (FIG. 8*d*1,*f*1) and only occasional intracellular bacteria were identified by 4 hpi. Bacterial net replication assays confirmed significantly increased numbers of wild-type *Salmonella* in enteroids at 1 hpi, versus those incubated with the mutant strain, and only the wild-type strain demonstrated significant net replication (FIG. 8*g*).

Influenza A Viruses that affect poultry are primarily respiratory pathogens, but will readily infect the intestines of many avian species. Invasion of PR8 (a mouse adapted H1N1 labstrain) into epithelial cells is the basis for virus replication and this process was confirmed in the chicken enteroids by confocal microscopy. Expression of viral nucleoprotein (NP) was detected within the epithelium of the enteroids at 24 hpi (FIG. 9). Viral replication in the enteroids was verified by measuring infectious virus titers in supernatant of infected enteroids, by plaque titration on MDCK cells. Titers increased from 0 to 48 hpi compared to mock infected controls (FIG. 9*d*).

The use of avian enteroids as models for viral infection is particularly advantageous as it provides for a model to study influenza infection. Some Influenza A virus strains survive and replicate in the intestine of waterfowls, spreading through fecal matter to cause an epidemic potential. Enteroids as discussed herein, for example chicken enteroids are considered to provide a representative experimental model for studying the gastrointestinal interactions of avian influenza virus in waterfowl. The inventors have detected H1N1 virus non-structural protein, NP, by immunofluorescence at 48 hpi throughout the organoid structures and confirmed replication through plaque assays, demonstrating PR8 successfully infected the enteroids and confirming these are capable models to recreate viral infection of the avian intestinal mucosa.

Successful Invasion of the *E. tenella* Sporozoites in Chicken Enteroids

The apicomplexan protozoa of the genus *Eimeria* are one of the major parasitic diseases of poultry. Following oral infection in vivo, the *E. tenella* sporozoites enter the caecal epithelial cells, migrate through the lamina propria to undergo multiple rounds of asexual multiplication at the base of the crypts, before eventually undergoing sexual multiplication. Since each developmental stage of *Eimeria* harbours a distinct number of parasitic divisions, the inventors used a combination of brightfield and fluorescence microscopy to determine whether the enteroid cultures could support parasite replication. In order to visualise the parasites, *E. tenella* sporozoites were stained with a fluorescent cell-membrane tracking dye, PKH67.

As shown in FIG. 10, at 1 day post-infection (dpi) sporozoites were identified in contact with the enteroid apical epithelial surface (FIG. 10*a*) and by 2 dpi they were observed inside enteroid cells (FIG. 10*b, c*). *E. tenella* subsequently divided within the enteroid cells (FIG. 10*d-f*), as determined by the size and increased number of PKH67+ parasites within a singular cell. The fluorescent membrane divisions in the enteroid cells correlated with what would be expected for distinct parasite life-cycle stages (FIG. 10*g*). To confirm the sexual replication stage was reached, expression of EtGAM56, which encodes a macrogamete specific protein incorporated into the oocyst wall, was demonstrated in *E. tenella* infected enteroids at 5, 7, and 9 dpi, but not at 2 dpi (FIG. 11).

Example 6

Epithelial Barrier Integrity and Cell Stress

The innermost layer of the intestinal luminal surface consists of a single cell thick epithelial lining which acts as a barrier, preventing the entry of harmful molecules and microbes while still allowing the selective passage of dietary nutrients, ions, and water. Tight junction proteins together with adherens junctions and desmosomes are essential gut epithelia barrier components which maintain physiological homeostasis. By immunostaining for two major cell-adhesion molecules and using TEM, the inventors demonstrated the presence of these junctions in chicken enteroids. Desmosomes and tight junctions (FIG. 5*a*) were visualised with TEM, adherens junctions were identified by intercellular E-cadherin expression (FIG. 5*b*) and the tight junction-associated protein ZO-1 was expressed in the epithelial layer (FIG. 5*c*). In order to determine whether the cell-cell junctions were functional, the enteroids were immersed in 4 kDa FITC-dextran. Enteroids treated with EDTA, which disrupts tight junctions, were used as a positive control. This analysis showed that untreated enteroids excluded the FITC-dextran, demonstrating mechanical integrity through intact intercellular junctions (FIG. 5*d*). The EDTA-treated enteroids, in contrast, allowed permeation of FITC-dextran through the intercellular spaces, indicating breakdown of the epithelial barrier (FIG. 5*e*).

Transcriptional analysis demonstrated that the enteroids expressed a large range of genes encoding components of mammalian focal adhesions, tight junctions, gap junctions, adherens junctions and desmosomes (FIG. 5*f*). Expression of these genes was generally stable throughout the culture period. In addition, although a range of cell-stress associated genes (derived from murine studies) were expressed in the enteroids, there was no significant evidence of modulation of their expression across the time points (FIG. 5*g*). Steady expression of both gene sets throughout the time-points is indicative of stable enteroid cultures over 7 days.

Floating chicken enteroids were found to develop and survive for a period of time. Without wishing to be bound by theory, it is considered that, for example with use of B27 media without additional exogenous growth and/or inhibitory factors, the cells in the isolated tissue and/or accompanying fibroblasts appear to initially supply the required factors for stem cell proliferation and propagation of intestinal epithelium. A unique feature of avian enteroids grown floating in culture is their 'inside-out' conformation, with the apical brush border facing the media. Intestinal stem cells contained within avian embryonic villi or mature crypts successfully self-organise to form enteroids with 3D multi-lobulated structures that mimic the in vivo architecture and differentiated cell-types of the in vitro avian intestinal epithelium.

Floating avian crypts rapidly orientate themselves so their basal epithelial surface rests on a dense central core of cells, thereby re-establishing integrin signalling. This positional change was not visualised in murine cultures and so the inventors consider this is an avian-specific phenomenon.

The inventors have demonstrated that the chicken enteroid in vitro model is closely akin to the in vivo intestine and will therefore provide more valuable data than single cell cultures as well as providing cost and ethical benefits to the poultry industry by avoiding the need for in vivo studies. The classical matrix-embedded enteroid, as determined for mammalian enteroids, possesses an internal lumen which proves limiting for host-pathogen studies where fragmenting the enteroids cannot guarantee the route of pathogen entry, and microinjections and monolayers add increasing layers of complexity and cost to the infection process. The novel externally accessible epithelial surface of the chicken enteroids allows for uncomplicated replication of the natural infection process.

The method to isolate crypts and derive differentiated enteroids with an accessible epithelial layer from the chicken small and large intestine as discussed herein allows for inexpensive and uncomplicated techniques to study host-pathogen interactions, pharmaceutical, nutritional, food additive and developmental studies.

As these enteroids reflect the 3D architecture and cellular composition of their in vivo counterparts they provide an effective in vitro model of the chicken intestinal epithelium.

Example 7—Immune Cell Component of Enteroid

Since embryonic enteroids develop from intestinal villi the inventors determined whether they also contained immune cells derived from the intestinal lamina propria. Using immunohistochemistry the inventors identified CD45+ leukocytes scattered throughout the central cell-dense core of the enteroids (FIG. 6*a-c*) and occasionally within the epithelium (FIG. 6*b*) at 2 days (FIGS. 6*a, b*) and 7 days (FIG. 6*c*) of culture. Subsequent immunostaining reflected the presence of cytoplasmic CD3+ cells, typical of NK cells which have been detected in embryos from ED14, CD4+ cells and CD8p+ cells (FIG. 6*d-f*). ChB6+ cells were identified which are indicative of both B cells and NK cells (FIG. 6*g*). Occasional chicken αβ1 TCR+(TCR2) and chicken αβ2 TCR+(TCR3) cells were found scattered through the enteroid lamina propria core (FIG. 6 *h-i*), appearing in the embryonic intestine a couple of days earlier than previous studies have reported. It is considered the could reflect breed variation or general changes to laying stock in the intervening 30 years of genetic selection. Embryonic chicken intestines cultured from CSF1R-reporter transgenic chicken embryos, which express eGFP in cells of the myeloid lineage, were used to visualise tissue mononuclear phagocyte. Imaging of CSF1R-eGFP transgenic chicken enteroids showed the presence of multiple CSF1R transgene+ cells, representing macrophages and dendritic cells, within the enteroid core at 2 days (FIGS. 6*j*) and 7 days (FIG. 6*k*, kl) of culture.

Further transcriptional analysis of mRNA from floating enteroids showed the expression of gene sets encoding various leukocytes of the mammalian enteric immune system (FIG. 6*l*), with relatively stable expression across the 7 days of culture. The inventors analyses confirmed strong expression of macrophage-related genes CSF1R, CTSB, LRP1, CKB, UQCRC1, PHB2 and HADHB. Gene-sets associated with NK cells, T cells, dendritic cells, and B cells were also represented, but their expression profiles suggest they are present in lower numbers than macrophages.

Uses of 3D Enteroids to Study Immune Responses after Interaction with Micro-Organisms and Pharmaceutical/Vaccine Components The inventors have determined methods to successfully differentiate self-organising, extensively budding avian enteroids that mimic the in vivo architecture and eplithelial characteristics of avian intestine without the use of a gel scaffold. Strikingly, the avian enteroids grown floating in culture adopt an "inside-out" confirmation, with the apical brush border facing the media. Additionally these enteroids comprise leukocytes that makes them a useful, natural epithelial-leukocyte co-culture model.

An example of the tests conducted on the enteroids provided by the invention which show that these are useful as a model system is discussed below.

Incubation of 3D enteroids with live *Salmonella Typhimurium*, wild type invasive bacteria and mutant non invasive resulted in upregulation of proinflammotory cytokine IL-6 mRNA (FIG. 12). As expected, purified LPS (lipopolysaccharides) derived from *Salmonella enterica* induced a modest increase in IL-6 but not IL-8 mRNA at 6 hours post stimulation. These data comparing induction of immune responses using live bacteria and purified LPS suggest that the 3D enteroids distinguish LPS from live bacteria (FIG. 13), micking the in vivo gut. Additional experiments in which enteroids are stimulated with other TLR agonists (viral and bacterial) or live pathogens have indicated responses micking the in vivo gut.

Although the invention has been particularly shown and described with reference to particular examples, it will be understood by those skilled in the art that various changes in the form and details may be made therein without departing from the scope of the present invention.

The invention claimed is:

1. An in vitro multilobulated three dimensional avian enteroid comprising multiple differentiated intestinal cell types of both epithelial and mesenchymal lineages, for use as a model of the avian intestine, wherein the enteroid comprises:

a. an inner core comprising lamina propria leukocytes, b. Intraepithelial leukocytes, and c. an exterior comprising an apical epithelial cell surface comprising differentiated intestinal epithelial cells bound by cell-cell junctions, with a morphology comprising villi and crypt structures.

2. The enteroid of claim 1, wherein the enteroid comprises intestinal stem cells, enterocytes, Paneth cells, goblet cells, enteroendocrine cells and leukocytes.

3. The enteroid of claim 1, wherein the enteroid is provided by culturing one or more chicken, turkey, duck or quail intestinal epithelial stem cells in suspension, without the use of a gel scaffold.

4. The enteroid of claim 1, wherein the enteroid is provided by culturing one or more avian intestinal epithelial stem cells in suspension, without the use of a gel scaffold.

5. The enteroid of claim 1, wherein the enteroid is provided by culturing one or more avian intestinal epithelial stem cells isolated from one of:

a. villi and/or crypt tissues, b. intestinal fragments containing stem cells, c. embryonic intestinal epithelial tissue, d. embryonic intestinal lining, optionally embryonic villi or crypt intestinal epithelial tissue, or e. neonate, juvenile or adult intestinal epithelial tissues.

* * * * *